US008354384B2

(12) United States Patent
Slack et al.

(10) Patent No.: US 8,354,384 B2
(45) Date of Patent: Jan. 15, 2013

(54) ANTI-AGING MICRORNAS

(75) Inventors: Frank J. Slack, Guilford, CT (US); Michelle M. Boehm, New Haven, CT (US)

(73) Assignee: Yale University, New Haven, CT (US)

( * ) Notice: Subject to any disclaimer, the term of this patent is extended or adjusted under 35 U.S.C. 154(b) by 968 days.

(21) Appl. No.: 11/426,292

(22) Filed: Jun. 23, 2006

(65) Prior Publication Data

US 2007/0287678 A1 Dec. 13, 2007

Related U.S. Application Data

(60) Provisional application No. 60/693,395, filed on Jun. 23, 2005.

(51) Int. Cl.
*A16K 48/00* (2006.01)
(52) U.S. Cl. ...... 514/44; 536/24.5; 536/24.31; 536/24.1
(58) Field of Classification Search .................. None
See application file for complete search history.

(56) References Cited

U.S. PATENT DOCUMENTS

| | | | |
|---|---|---|---|
| 3,832,253 A | 8/1974 | Di Palma et al. |
| 3,854,480 A | 12/1974 | Zaffaroni |
| 4,452,775 A | 6/1984 | Kent |
| 4,667,013 A | 5/1987 | Reichle |
| 4,675,189 A | 6/1987 | Kent et al. |
| 4,748,034 A | 5/1988 | de Rham |
| 5,075,109 A | 12/1991 | Tice et al. |
| 5,133,974 A | 7/1992 | Paradissis et al. |
| 5,223,618 A | 6/1993 | Cook et al. |
| 5,239,660 A | 8/1993 | Ooi |
| 5,272,071 A | 12/1993 | Chappel |
| 5,378,825 A | 1/1995 | Cook et al. |
| 5,407,686 A | 4/1995 | Patel et al. |
| 5,466,786 A | 11/1995 | Buhr et al. |
| 5,489,743 A | 2/1996 | Robinson et al. |
| 5,578,461 A | 11/1996 | Sherwin et al. |
| 5,602,240 A | 2/1997 | De Mesmaeker et al. |
| 5,610,289 A | 3/1997 | Cook et al. |
| 5,614,617 A | 3/1997 | Cook et al. |
| 5,672,697 A | 9/1997 | Buhr et al. |
| 5,705,629 A | 1/1998 | Bhongle |
| 5,714,606 A | 2/1998 | Acevedo et al. |
| 5,736,152 A | 4/1998 | Dunn |
| 5,777,092 A | 7/1998 | Cook et al. |
| 5,858,988 A | 1/1999 | Wang |
| 6,919,208 B2 | 7/2005 | Levy et al. |

FOREIGN PATENT DOCUMENTS

| | | |
|---|---|---|
| WO | WO 84/03564 | 9/1984 |
| WO | WO 91/06667 | 5/1991 |
| WO | WO 91/09955 | 7/1991 |
| WO | WO 92/20808 | 11/1992 |
| WO | WO 93/09222 | 5/1993 |
| WO | WO 94/12650 | 6/1994 |
| WO | WO 94/28122 | 12/1994 |

OTHER PUBLICATIONS

Sempere et al. Expression profiling of mammalian microRNAs uncovers a subset of brain-expressed microRNAs with possible roles in murine and human neuronal differentiation. Genome Biology 2004, vol. 5:R13.*
Lee et al. Depletion of human micro-RNA mir-125b reveals that it is critical for the proliferation of differentiated cells but not for the dow-regulation of putative targets during differentiation. J. Biological Chemistry 2005, vol. 280: 16635-16641.*
Baugh et al. DAF-16/FOXO regulates transcription of cki-1/Cip/Kip and repression of lin-4 during C. elegans L1 arrest. Current Biology 16, 780-785, Apr. 18, 2006.*
Abrahante, et al., "The *Caenorhabditis elegans* hunchback-like gene lin-57/hbl-1 controls developmental time and is regulated by microRNAs", *Dev. Cell*, 4(5):625-37 (2003).
Ahrendt, et al., "Cigarette smoking is strongly associated with mutation of the K-ras gene in patents with primary adenocarcinoma of the lung", *Cancer*, 92:1525-1530 (2001).
Akao, et al., "let-7 microRNA functions as a potential growth suppressor in human colon cancer cells", *Biol. Pharm. Bull.*, 29(5):903-6 (2006).
Ambros and Horvitz, "Heterochronic mutants of the nematode *Caenorhabditis elegans*", *Science*, 226(4673):409-16(1984).
Ambros, "Cell cycle-dependent sequencing of cell fate decisions in *Caenorhabditis elegans* vulva precursor cells", *Development*, 126:1947-1956 (1999).
Antebi, "The tick-tock of aging?", *Science*, 310:1911-1913 (2005).
Banerjee and Slack, "Control of developmental timing by small temporal RNAs: a paradigm for RNA-mediated regulation of gene expression", *Bioessays*, 24(2):119-29 (2002).
Bartel, MicroRNAs: genomics, biogenesis, mechanism, and function, *Cell*, 116(2):281-97 (2004).
Beitel, et al., "*Caenorhabditis elegans* ras gene let-60 acts as a switch in the pathway of vulval induction", *Nature*, 348(6301):503-509 (1990).

(Continued)

*Primary Examiner* — Kimberly Chong
(74) *Attorney, Agent, or Firm* — Pabst Patent Group LLP

(57) ABSTRACT

Methods and compositions for modulating aging genes or their targets for the treatment or prevention of senescence or symptoms thereof have been developed based on the discovery of naturally occurring inhibitory nucleic acids, in particular lin-4 miRNA, that downregulate genes involved in senescence, lifespan, or age-related disorders. Representative aging genes include, but are not limited to lin-4, lin-14, let-7, lin-28, egl-35 and lin-42. Methods for identifying modulators of aging genes and targets of aging genes are also provided. The disclosed compositions are useful as diagnostics. These can be used in assays to compare genes in normal individuals, with those who are aging well or who demonstrate early senescence, and with those who have age-related disorders such as Parkinson's and Alzheimer's. The genes can be used to study the pathways and mechanisms involved in aging and age-related disorders. These genes can be used as drug targets, or in drug design, to develop drugs that can inhibit one or more characteristics of senescence or age-related disorders. These compositions should be effective therapies for treating or slowing the effects of one or more symptoms or characteristics of age-related disorders resulting from activation or over-expression of aging genes. Compositions that alter the expression of particular aging genes affecting the insulin-like signal pathway are described. Suitable compositions described herein include, inhibitory nucleic acids and small molecules, in particular miRNA.

28 Claims, 13 Drawing Sheets

OTHER PUBLICATIONS

Berset, et al., "Notch inhibition of RAS signaling through MAP kinase phosphatase LIP-1 during *C. elegans* vulval development", *Science*, 291:1055-1058 (2001).

Boehm and Slack, "A developmental timing microRNA and its target regulate life span in *C. elegans*", *Science*, 310:1954-1957 (2005).

Brennecke, et al., "Bantam encodes a developmentally regulated microRNA that controls cell proliferation and regulates the proapoptotic gene hid in Drosophila", *Cell*, 113(1):25-36 (2003).

Brummelkamp, et al., "Stable suppression of tumorigenicity by virus-mediated RNA interference", *Cancer Cell*, 2(3):243-7 (2002).

Calin, et al., "Frequent deletions and doenregulation of microRNA genes *miR*15 and *miR*16 at 13q14 in chronic lymphocytic leukemia", *Proc Natl Aced Sci U S A*, 99(24):15524-9 (2002).

Calin, et al., "Human microRNA gene are frequently located at fragile sites and genomic regions involved in cancers", *Proc Natl Aced Sci U S A*, 101:2999-3004 (2004).

Capecchi, "Altering the genome by homologous recombination", *Science*, 244:1288-1292 (1989).

Carmell, et al., "The Argonaute family: tentacles that reach into RNAi, developmental control, stem cell maintenance, and tumorigenesis", *Genes Dev.*, 16(21):2733-42 (2002).

Caudy, et al., "A micrococcal nuclease homologue in RNAi effector complexes", *Nature*, 425(6956):411-4 (2003).

Ceol and Horvitz, "A new class of *C. elegans* synMuv genes implicates a Tip60/NuA4-like HAT complex as a negative regulator of Ras signaling", *Dev Cell*, 6:563-576 (2004).

Chang, et al., "MicroRNAs act sequentially and asymmetrically to control chemosensory laterality in the nematode", *Nature*, 430(7001):785-9 (2004).

Chen, et al., "MicroRNAs Modulate HematopoieticLineage Differentiation", *Science*, 303(5654):83-6 (2004).

Chen, et al., "The developmental miRNA profiles of zebrafish as determined by small RNA cloning", *Genes Dev.*, 19(11):1288-93 (2005).

Dent and Han, "Post-embryonic expression pattern of *C. elegans* let-60 ras reporter constructs", *Mech Dev*, 72:179-182 (1998).

Duursma and Agami, "Ras interference as cancer therapy", *Semin. Cancer Biol.*, 13(4):267-73 (2003).

Eisenmann and Kim, "Mechanism of activation of the *Caenorhabditis elegans* ras homologue let-60 by a novel, temperature-sensitive, gain-of-function mutation", *Genetics*, 146:553-565 (1997).

Feinbaum and Ambros, "The timing of lin-4 RNA accumulation controls the timing of postembryonic developmental events in *Caenorhabditis elegans*", *Dev. Biol.*, 210(1):87-95(1999).

Freemont, "The RING finger. A novel protein sequence motif related to the zinc finger", *Ann. New York. Acad. Sci.*, 684:174-192 (1993).

Garigan, et al., "Genetic analysis of tissue aging in *Caenorhabditis elegans*: a role for heat-shock factor and bacterial proliferation", *Genetics*, 161(3), 1101-12 (2002).

Gauwerky, et al., "Activation of MYC in a masked t(8;17) translocation results in an aggressive B-cell leukemia", *Proc Natl Acad Sci U S A*, 86(22):8867-71 (1989).

Giovanella, et al., Heterotransplantation of human malignant tumors in "nude" thymusless mice. II. Malignant tumors induced by injection of cell cultures derived from human solid tumors, *J. Natl. Can. Inst.*, 52:921-30 (1974).

Grishok, et al., "Genes and mechanisms related to RNA interference regulate expression of the small temporal RNAs that control *C. elegans* developmental timing", *Cell* 106(1):23-34 (2001).

Grosshans, et al., "The temporal patterning microRNA let-7 regulates several transcription factors at the larval to adult transition in *C. elegans*", *Dev. Cell* 8(3)321-30(2005).

Haasch, et al., "T cell activation induces a noncoding RNA transcript sensitive to inhibition by immunosuppressant drugs and encoded by the proto-oncogene, BIC", *Cell Immunol*, 217(1-2):78-86 (2002).

Hamilton and Baulcombe, "A species of small antisense RNA in posttranscriptional gene silencing in plants", *Science*, 286(5441):950-2 (1999).

Han and Sternberg, "let-60, a gene that specifies cell fates during *C. elegans* vulval induction, encodes a ras protein", *Cell*, 63:921-931 (1990).

Han, et al., "The let-60 locus controls the switch between vulval and nonvulval cell fates in *Caenorhabditis elegans*", *Genetics*, 126:899-913 (1990).

Hasegawa, et al., "RING finger motif regulates transforming activity of the rfp/ret fusion gene", *Biochem Biophys Res Commun*, 225(2):627-31 (1996).

He, et al., "A microRNA polycistron as a potential human oncogene", *Nature*, 435(7043):828-33 (2005).

Hopper, et al., "ARK-1 inhibits EGFR signaling in *C. elegans*", *Mol Cell*, 6:65-75 (2000).

Hsu, et al., "Regulation of aging and age-related disease by DAF-16 and heat-shock factor", *Science*, 300(5622):1142-5 (2003).

Huang, et al., "Functional silencing of hepatic microsomal glucose-6-phosphatase gene expression in vivo by adenovirus-mediated delivery of short hairpin RNA", *FEBS Lett.*, 558(1-3):69-73 (2004).

Hutvagner and Zamore, "A microRNA in a multiple-turnover RNAi enzyme complex", *Science*, 297(5589):2056-60 (2002).

Hutvagner, et al., "A cellular function for the RNA-interference enzyme Dicer in the maturation of the let-7 small temporal RNA", *Science*, 293(5531):834-8 (2001).

Hutvagner, et al., "Sequence-specific inhibition of small RNA function", *PLoS Biol*, 2(4):04 65-0475 (2004).

Johnson, et al., "RAS is regulated by the let-7 microRNA family", *Cell*, 120(5):635-47(2005).

Johnson, et al., "Somatic activation of the *K-ras* oncogene causes early onset lung cancer in mice", *Nature*, 410:1111-1116 (2001).

Johnson, et al., "The time of appearance of the *C. elegans let-7* microRNA is transcriptionally controlled utilizing a temporal regulatory element in its promoter", *Dev Biol*, 259:364-379 (2003).

Johnston and Hobert, "A microRNA controlling left/right neuronal asymmetry in *Caenorhabditis elegans*", *Nature*, 426(6968):845-9 (2003).

Kakizuka, et al., "Chromosomal translocation t(15;17) in human acute promyelocytic leukemia fuses RAR alpha with a novel putative transcription factor, PML", *Cell*, 66:663-674 (1991).

Karube, et al., "Reduced expression of Dicer associated with poor prognosis in lung cancer patients", *Cancer Sci*, 96(2):111-5 (2005).

Katz, et al., "Different levels of the *C. elegans* growth factor LIN-3 promote distinct vulval precursor fates", *Cell*, 82:297-307 (1995).

Kawasaki and Taira, "Short hairpin type of dsRNAs that are controlled by tRNA(Val) promoter significantly induce RNAi-mediated gene silencing in the cytoplasm of human cells", *Nucleic Acids Res.*, 31(2):700-7 (2003).

Kenyon, et al., "A *C. elegans* mutant that lives twice as long as wild type", *Nature*, 366(6454):461-4 (1993).

Lagos-Quintana, et al., "Identification of novel genes coding for small expressed RNAs", *Science*, 294(5543):853-8 (2001).

Lagos-Quintana, et al., "Identification of tissue-specific microRNAs from mouse", *Curr. Biol.*, 12(9):735-9 (2002).

Lagos-Quintana, et al., "New microRNAs from mouse and human", *RNA*, 9(2):175-179 (2003).

Lai, et al., "Pervasive regulation of *Drosophila* Notch target genes by GY-box-, Brd-box-, and K-box-class microRNAs", *Genes Dev.*, 19(9):1067-80 (2005).

Lau, et al., "An abundant class of tiny RNAs with probable regulatory roles in *Caenorhabditis elegans*", *Science*, 294(5543):858-62 (2001).

Le Douarin, et al., "The N-terminal part of TIF1, a putative mediator of the ligand-dependent activation function (AF-2) of nuclear receptors, is fused to B-raf in the oncogenic protein T18", *EMBO J.*, 14(9):2020-2033 (1995).

Lecellier, et al., "A cellular microRNA mediates antiviral defense in human cells", *Science*, 308(5721):557-60 (2005).

Lee and Ambros, "An extensive class of small RNAs in *Caenorhabditis elegans*", *Science*, 294(5543):862-4 (2001).

Lee, et al., "Depletion of human micro-RNA miR-125b reveals that it is critical for the proliferation of differentiated cells but not for the down-regulation of putative targets during differentiation", *Jour. Biol. Chem.*, 280(17):16635-16641 (2005).

Lee, et al., "The *C. elegans* heterochronic gene lin-4 encodes small RNAs with antisense complementarity to lin-14", *Cell*, 75(5):843-854 (1993).

Lee, et al., "The nuclear RNase III Drosha initiates microRNA processing", *Nature*, 425(6956):415-9 (2003).
Lee, et al., "unc-101, a gene required for many aspects of *Caenorhabditis elegans* development and behavior, encodes a clathrin-associated protein", *Genes Dev.*, 8:60-73 (1994).
Li, et al., "A modified Boyden Chamber assay for tumor cell transendothelial migration in vitro", *Clin. Exp. Metastasis*, 17:423-9 (1999).
Li, et al., "Expression of the putative proto-oncogene His-1 in normal and neoplastic tissues", *Am J Pathol*, 150:1297-305 (1997).
Lim, et al., "The microRNAs of *Caenorhabditis elegans*", *Genes Dev.*, 17(8):991-1008 (2003).
Lin, et al., "Regulation of the *Caenorhabitits elegans* longevity protein DAF-16 by insulin/IGF-1 and germline signaling", *Nature Genetics*, 28:139-145 (2001).
Lin, et al., "The *C. elegans* hunchback homolog, hbl-1, controls temporal patterning and is a probable microRNA target", *Dev. Cell*, 4(5):639-50 (2003).
Liu, et al., "Regulation of signaling genes by TGFbeta during entry into dauer diapause in *C. elegans*", *BMC Developmental Biology*, 4:11 (2004).
Lorenz, et al., "Steroid and lipid conjugates of siRNAs to enhance cellular uptake and gene silencing in liver cells", *Bioorg. Med. Chem. Lett.*, 14(19):4975-4977 (2004).
Lu, et al., "Gene regulation and DNA damage in the ageing human brain", *Nature*, 429(6994), 883-91 (2004).
Lu, et al., "MicroRNA expression profiles classify human cancers", *Nature*, 435(7043):834-838 (2005).
Ma, et al., "Nuclease-resistant external guide sequence-induced cleavage of target RNA by human ribonuclease P", *Antisense Nucleic Acid Drug Dev.* 8:415-426 (1998).
Malumbres, et al., "RAS oncogenes: the first 30 years", *Nat Rev Cancer*, 3(6):459-65 (2003).
McCarroll, et al., "Comparing genomic expression patterns across species identifies shared transcriptional profile in aging", *Nat. Genet.*, 36(2):197-204 (2004).
McKay, et al., "Transformation and stimulation of DNA synthesis in NIH-3T3 cells are a titratable function of normal p21N-ras expression", *Embo J*, 5:2617-2621 (1986).
McManus, "MicroRNAs and cancer", *Seminars in Cancer Biology*, 13:253-258 (2003).
Meister, et al., "Sequence-specific inhibition of microRNA- and siRNA-induced RNA silencing", *RNA*, 10:544-550 (2004).
Meng, et al., "Automated docking with grid-based energy evaluation", *J. Comp. Chem.*, 13:505-524 (1992).
Michael, et al., "Reduced accumulation of specific microRNAs in colorectal neoplasia", *Mol Cancer Res*, 1(12):882-91 (2003).
Moss, et al., "The cold shock domain protein LIN-28 controls developmental timing in *C. elegans* and is regulated by the lin-4 RNA", *Cell* 88(5):637-46(1997).
Mourelatos, et al., "miRNPs: a novel class of ribonucleoproteins containing numerous microRNAs", *Genes Dev.*, 16(6):720-8 (2002).
Nyce and Metzger, "DNA antisense therapy for asthma in an animal model", *Nature*, 385:721-725 (1997).
O'Donnell, et al., "c-Myc-regulated microRNAs modulate E2F1 expression", *Nature*, 435(7043):839-43 (2005).
Olsen and Ambros, "The lin-4 regulatory RNA controls developmental timing in *Caenorhabditis elegans* by blocking LIN-14 protein synthesis after the initiation of translation", *Dev. Biol.*, 216(2):671-80 (1999).
Pardridge, "Intravenous, non-viral RNAi gene therapy of brain cancer", *Expert Opin. Biol. Ther.*, 4(7):1103-13 (2004).
Pasquinelli, et al., "Conservation of the sequence and temporal expression of let-7 heterochronic regulatory RNA", *Nature*, 408(6808):86-9 (2000).
Pilkington, et al., "In vitro and in vivo models for the study of brain tumour invasion", *Anticancer Res.*, 17:4107-9 (1997).
Poy, et al., "A pancreatic islet-specific microRNA regulates insulin secretion", *Nature*, 432(7014):226-30 (2004).
Pulciani, et al., "Ras gene Amplification and malignant transformation", *Mol Cell Biol*, 5:2836-2841 (1985).
Reinhart, et al., "MicroRNAs in plants", *Genes and Dev.*, 16:1616-1626 (2002).

Reinhart, et al., "The 21-nucleotide let-7 RNA regulates developmental timing in *Caenorhabditis elegans*", *Nature*, 403:901-906 (2000).
Ribatti, et al., "The chick embryo chorioallantoic membrane as a model for in vivo research on angiogenesis", *Intl. J. Dev. Biol.*, 40:1189-97 (1999).
Rump, et al., "Modification of the plasma clearance and liver uptake of steroid ester-conjugated oligodeoxynucleotides by association with (lactosylated) low-density lipoprotein", *Biochem. Pharmacol.*, 59(11):1407-1416 (2000).
Ruvkun et al., "The *Caenorhabditis elegans* heterochronic gene lin-14 encodes a nuclear protein that forms a temporal developmental switch", *Nature*, 338(6213):313-9 (1989).
Schneider, et al., "Building blocks for oligonucleotide analogs with dimethylene-sulfide, -sulfoxide and -sulfone groups replacing phosphodiester linkages", *Tetrahedron Lett.*, 31:335-38 (1990).
Slack and Ruvkun, "Temporal pattern formation by heterochronic genes", *Annu. Rev. Genet.*, 31:611-34 (1997).
Slack, et al., "The lin-41 RBCC gene acts in the *C. elegans* heterochronic pathway between the let-7 regulatory RNA and the LIN-29 transcription factor", *Molec. Cell*, 5:659-669 (2000).
Soutschek, et al., "Therapeutic silencing of an endogenous gene by systemic administration of modified siRNAs", *Nature*, 432:173-178 (2004).
Stein, et al., "The genome sequence of *Caenorhabditis briggsae*: A platform for comparative genomics", *PLoS Biol*, 1(2):166-192 (2003).
Sternberg, "Lateral inhibition during vulval induction in *Caenorhabditis elegans*", *Nature*, 335:551-554 (1988).
Sullivan, et al., "SV40-encoded microRNAs regulate viral gene expression and reduce susceptibility to cytotoxic T cells", *Nature*, 435(7042):682-6 (2005).
Sulston and Horvitz, "Post embryonic cell lineages of the nematode *Caenorhabditis elegans*", *Dev Biol*, 56:110-156 (1977).
Takamizawa, et al., "Reduced expression of the let-7 microRNAs in human lung cancers in association with shortened postoperative survival", *Cancer Res*, 64:3753-3756 (2004).
Tam, et al., "Avian bic, a gene isolated from a common retroviral site in avian leukosis virus-induced lymphomas that encodes a noncoding RNA, cooperates with c-myc in lymphomagenesis and erythroleukemogenesis", *J Virol*, 76:4275-4286, (2002).
Tan, et al., "MAP kinase signaling specificity mediated by the LIN-1 Ets/LIN-31 WH transcription factor complex during *C. elegans* vulval induction", *Cell* , 93:569-580 (1998).
Timmons, et al., "Ingestion of bacterially expressed dsRNAs can produce specific and potent genetic interference in *Caenorhabditis elegans*", *Gene*, 263:103-112 (2001).
Tissenbaum and Guarente, "Model organisms as a guide to mammalian aging", *Dev. Cell*, 2(1), 9-19 (2002).
Uhlmann, et al., "Antisense oligonucleotides: A new therapeutic principle", *Chem. Rev.*, 90:543-584 (1990).
Vella, et al., "The *C. elegans* microRNA let-7 binds to imperfect let-7 complementary sites from the lin-41 3'UTR", *Genes Dev.*, 18(2):132-7 (2004).
Wang and Sternberg, "Pattern formation during *C. elegans* vulval induction", *Curr Top Dev Biol*, 51:189-220 (2001).
Wasserman, et al., "The evolution of B precursor leukemia in the Emu-ret mouse", *Blood*, 92(1):273-82 (1998).
Wienholds, et al., "MicroRNA expression in zebrafish embryonic development", *Science*, 309(5732):310-1 (2005).
Wightman, et al., "Negative regulatory sequences in the lin-14 3'-untranslated region are necessary to generate a temporal switch during *Caenorhabditis elegans* development", *Genes Dev.*, 5(10):1813-24 (1991).
Wightman, et al., Posttranscriptional regulation of the heterochronic gene lin-14 by lin-4 mediates temporal pattern formation in *C. elegans, Cell*, 75(5):855-862 (1993).
Xu, et al., "The *Drosophila* MicroRNA Mir-14 Suppresses Cell Death and Is Required for Normal Fat Metabolism", *Curr Biol*, 13(9):790-5 (2003).

Yang, et al., "Silencing of H-ras gene expression by retrovirus-mediated siRNA decreases transformation efficiency and tumorgrowth in a model of human ovarian cancer", *Oncogene*, 22(36):5694-701 (2003).

Yekta, et al., "MicroRNA-directed cleavage of HOXB8 mRNA", *Science*, 304(5670):594-6 (2004).

Yoo, et al., "Crosstalk between the EGFR and Lin-12/Notch pathways in *C. elegans* vulval development", *Science*, 303:663-666 (2004).

Yoon, et al., "Similarity of sli-1, a regulator of vulval development in *C. elegans*, to the mammalian proto-oncogene c-cbl", *Science*, 269:1102-1105 (1995).

Zeng, et al., "Both natural and designed micro RNAs can inhibit the expression of cognate mRNAs when expressed in human cells", *Mol. Cell*, 9(6):1327-33 (2002).

Zeng, et al., "MicroRNAs and small interfering RNAs can inhibit mRNA expression by similar mechanisms", *Proc. Natl. Acad. Sci. U.S.A.*, 100(17):9779-84 (2003).

Zhang, et al., "Intravenous RNA interference gene therapy targeting the human epidermal growth factor receptor prolongs survival in intracranial brain cancer", *Clin. Cancer Res.*, 10(11):3667-77 (2004).

\* cited by examiner

SEQUENCE LISTING

<160> NUMBER OF SEQ ID NOS: 15

<210> SEQ ID NO 1
<211> LENGTH: 21
<212> TYPE: RNA

<210> SEQ ID NO 1
<211> LENGTH: 21
<212> TYPE: RNA
<213> ORGANISM: Caenorhabditis elegans

<400> SEQUENCE: 1
ucccugagac cucaagugug a                                          21

<210> SEQ ID NO 2
<211> LENGTH: 693
<212> TYPE: DNA
<213> ORGANISM: Caenorhabditis elegans

<400> SEQUENCE: 2

| | | | | |
|---|---|---|---|---|
| gtcgacgaga | cgccgagtct | cccttactgc | aaaaatgaga | ggggagcgag gtggtctacg | 60 |
| tctctgtggc | acctaacact | atttcgggga | cgcgtcgcca | agcggtggtg gtgccagcct | 120 |
| cacggaaagg | cttgcggggc | gcccggctcg | tgtccctccg | tgctctgctg cgtgtgcctt | 180 |
| ccgcttctcg | tctgtcctct | ctctcagtgc | gcgggggac | cgcggcaaaa aagaataacg | 240 |
| acgaagcgac | cgaatgaccc | agtctcttca | cttctctact | ttcgatcctc ctccttcagc | 300 |
| tactcctccc | atgtccatcc | atcctccgcc | ccatcactcc | cagagaccct tcggtcact | 360 |
| ctttccaata | gactctacca | caatcggtcg | gactcatcac | acttaccttt caaatatcta | 420 |
| aactattcct | gaatataata | aatcttatag | tttttagatt | ctagacaatt tctagagttt | 480 |
| tggttggttt | atgagtttat | gcttccggcc | tgttccctga | gacctcaagt gtgagtgtac | 540 |
| tattgatgct | tcacacctgg | gctctccggg | taccaggacg | gtttgagcag atcttttttt | 600 |
| ctgttttcac | ggggttttt | ttcacactgg | gagctagttc | caataaaatg gtattcgggg | 660 |
| aaaagggtca | aacgattatt | ttcagaagtc | gac | | 693 |

<210> SEQ ID NO 3
<211> LENGTH: 1729
<212> TYPE: DNA
<213> ORGANISM: Caenorhabditis elegans

<400> SEQUENCE: 3

| | | | | |
|---|---|---|---|---|
| atttaactcc | aactgttcac | cacgtcactt | tgacaccacg | atccagccta atttggaccg | 60 |
| tgaactatac | gatctacgta | gttgtccttc | tgcccaatca | agcctttctg ttgtcatgga | 120 |
| tctgcctgga | acgtcttcga | acgatttcgt | tcaaccgttt | tcaacatttt atccatcgcc | 180 |
| gacgtcgccg | ccaatgcacc | aagctgccct | cttgccagcc | cttacagctc tctatcctca | 240 |
| actactacaa | ttgccacact | taaaatctga | ttatttgata | cgatcagata tgagcgcttt | 300 |
| caaagaagta | accgatcttc | gacaagcagt | gaatttgata | ctgcctatgt acctttgta | 360 |
| tccaactatt | ggaaatggat | tcaatgcgac | aggattggca | gcacagccaa ctctacagca | 420 |
| tgtgatacag | cagagtttgt | tacgcaaacg | acctgtagct | caaacaccaa ccgttccaca | 480 |
| gcccgagtgc | ccgggtcaga | tacggccagt | tttaagctca | cccgctgcag cattgcaaaa | 540 |
| cgtaataatg | ttgaacccat | ggataatggg | atcatcattg | aaaccagcat cgccgacatt | 600 |
| acctaatgga | caaataccaa | caacaattgg | tgagacatct | cttcaaggta cagatgacca | 660 |
| gacagtcaaa | tggataggcc | cttccagcgt | ggatagtaat | ggcacagaaaa ctgacagttc | 720 |
| tgcagcttcc | gcaggcgaca | atcaaaacat | tgacgtaatt | ggcgatggca gtgaatcgcc | 780 |
| gacctcttca | aatcacagcg | cacaggaaat | tgctctcatg | acgtctcaac aaacatttct | 840 |
| gaatgcttta | aaggattctt | cgttttttatt | cacaaatcca | gtaccaacag ttgaaacagc | 900 |
| tccaccactc | cgtgttgccc | caccaatcaa | tggaacaaca | aacggaactg ctaaggctgg | 960 |
| tggtccagaa | cgaaaaccaa | ggaaaccagt | gaatgacgac | attgtcaaaa ttgttaggaa | 1020 |

```
tcaagatttg agcgaggaga atatttcaat gttcgaaatc cccgttccaa aagcaatagc    1080
atctgatcca actttccgac cagtgtcaga acaacaaatt attcaacaga tcattcaagg    1140
caaaaagtat gaagagatgg aagttggtga atgcatgatt cagctttgta agaagttagc    1200
agaaaagcgt gtctttggac cacgtctcat gtcacaaacc acagttgctg gtctcaacca    1260
ctcgaactat gcaaatcttc caatcaaagg aatttgctat attcaacatg tctgtagaaa    1320
agtcttatat gacaagtttg aaaacgagga agacttttgg gacaaattcc gcgaggcaat    1380
gcgcaaattg gcagccagat gtcgcagagt taggcatgcc aaaaagacaa acacaacag    1440 agaagaggct caggcagaaa tgttaagcaa aagatatgga aagatatgc cgttcaattt    1500 gaacggagct ggtttgataa ggcccaaagt ggaaacagta tcgcctgaag ctaacatctt    1560
gaatagcgat caaataaaga gccagcttga aagtttatttt gcacatattc caaaaactga    1620
gagcgaaacg ccactaattg aaataattca acaaaacatc agtctcttca cccatcttat    1680
ccgaactaaa gtggaatcac aatctcctcc tcttcaaggt ccacaatag              1729
```

<210> SEQ ID NO 4
<211> LENGTH: 537
<212> TYPE: PRT
<213> ORGANISM: Caenorhabditis elegans

<400> SEQUENCE: 4

```
Met Asp Leu Pro Gly Thr Ser Ser Asn Asp Phe Val Gln Pro Phe Ser
1               5                   10                  15

Thr Phe Tyr Pro Ser Pro Thr Ser Pro Pro Met His Gln Ala Ala Leu
            20                  25                  30

Leu Pro Ala Leu Thr Ala Leu Tyr Pro Gln Leu Leu Gln Leu Pro His
        35                  40                  45

Leu Lys Ser Asp Tyr Leu Ile Arg Ser Asp Met Ser Ala Phe Lys Glu
    50                  55                  60

Val Thr Asp Leu Arg Gln Ala Val Asn Leu Ile Leu Pro Met Leu Pro
65                  70                  75                  80

Leu Tyr Pro Thr Ile Gly Asn Gly Phe Asn Ala Thr Gly Leu Ala Ala
                85                  90                  95

Gln Pro Thr Leu Gln His Val Ile Gln Gln Ser Leu Leu Arg Lys Arg
            100                 105                 110

Pro Val Ala Gln Thr Pro Thr Val Pro Gln Pro Glu Cys Pro Gly Gln
        115                 120                 125

Ile Arg Pro Val Leu Ser Ser Pro Ala Ala Leu Gln Asn Val Ile
    130                 135                 140

Met Leu Asn Pro Trp Ile Met Gly Ser Ser Leu Lys Pro Ala Ser Pro
145                 150                 155                 160

Thr Leu Pro Asn Gly Gln Ile Pro Thr Thr Ile Gly Glu Thr Ser Leu
                165                 170                 175

Gln Gly Thr Asp Asp Gln Thr Val Lys Trp Ile Gly Pro Ser Ser Val
            180                 185                 190

Asp Ser Asn Gly Gln Lys Thr Asp Ser Ala Ala Ser Ala Gly Asp
        195                 200                 205

Asn Gln Asn Ile Asp Val Ile Gly Asp Gly Ser Glu Ser Pro Thr Ser
    210                 215                 220

Ser Asn His Ser Ala Gln Glu Ile Ala Leu Met Thr Ser Gln Gln Thr
225                 230                 235                 240

Phe Leu Asn Ala Leu Lys Asp Ser Ser Phe Leu Phe Thr Asn Pro Val
                245                 250                 255
```

```
Pro Thr Val Glu Thr Ala Pro Leu Arg Val Ala Pro Ile Asn
            260                 265                 270
Gly Thr Thr Asn Gly Thr Ala Lys Ala Gly Gly Pro Glu Arg Lys Pro
                275                 280                 285
Arg Lys Pro Val Asn Asp Asp Ile Val Lys Ile Val Arg Asn Gln Asp
            290                 295                 300
Leu Ser Glu Glu Asn Ile Ser Met Phe Glu Ile Pro Val Pro Lys Ala
305                 310                 315                 320
Ile Ala Ser Asp Pro Thr Phe Arg Pro Val Ser Glu Gln Ile Ile
                325                 330                 335
Gln Gln Ile Ile Gln Gly Lys Lys Tyr Glu Met Glu Val Gly Glu
            340                 345                 350
Cys Met Ile Gln Leu Cys Lys Lys Leu Ala Glu Lys Arg Val Phe Gly
                355                 360                 365
Pro Arg Leu Met Ser Gln Thr Thr Val Ala Gly Leu Asn His Ser Asn
            370                 375                 380
Tyr Ala Asn Leu Pro Ile Lys Gly Ile Cys Tyr Ile Gln His Val Cys
385                 390                 395                 400
Arg Lys Val Leu Tyr Asp Lys Phe Glu Asn Glu Glu Asp Phe Trp Asp
                405                 410                 415
Lys Phe Arg Glu Ala Met Arg Lys Leu Ala Ala Arg Cys Arg Arg Val
            420                 425                 430
Arg His Ala Lys Lys Thr Lys His Asn Arg Glu Glu Ala Gln Ala Glu
            435                 440                 445
Met Leu Ser Lys Arg Tyr Gly Glu Asp Met Pro Phe Asn Leu Asn Gly
            450                 455                 460
Ala Gly Leu Ile Arg Pro Lys Val Glu Thr Val Ser Pro Glu Ala Asn
465                 470                 475                 480
Ile Leu Asn Ser Asp Gln Ile Lys Ser Gln Leu Glu Ser Leu Phe Ala
                485                 490                 495
His Ile Pro Lys Thr Glu Ser Glu Thr Pro Leu Ile Glu Ile Ile Gln
            500                 505                 510
Gln Asn Ile Ser Leu Phe Thr His Leu Ile Arg Thr Lys Val Glu Ser
            515                 520                 525
Gln Ser Pro Pro Leu Gln Gly Pro Gln
530                 535

<210> SEQ ID NO 5
<211> LENGTH: 23
<212> TYPE: RNA
<213> ORGANISM: homo sapiens

<400> SEQUENCE: 5
ucccugagac ccuuuaaccu gug                                              23

<210> SEQ ID NO 6
<211> LENGTH: 22
<212> TYPE: RNA
<213> ORGANISM: Homo sapiens

<400> SEQUENCE: 6
ucccugagac ccuaacuugu ga                                               22

<210> SEQ ID NO 7
<211> LENGTH: 22
<212> TYPE: DNA
<213> ORGANISM: Caenorhabditis elegans
```

```
<400> SEQUENCE: 7
tgaggtagta ggttgtatag tt                                            22

<210> SEQ ID NO 8
<211> LENGTH: 1212
<212> TYPE: DNA
<213> ORGANISM: Caenorhabditis elegans

<400> SEQUENCE: 8
gatgtcgacg gtagtatcgg aggaaggaa tgatgggaat aaccgatatt caccacaaga     60
tgaagttgaa gataggctgc cagatgtagt tgacaatagg cttactgaga acatgagagt   120
tccttccttc gagaggctcc cgtcaccaac acctcgatac tttggctcat gcaaatggtt   180
taatgtgtcg aaaggatatg gttttgtgat cgatgacatc accggtgaag atctattcgt   240
tcatcagtct aatctcaata tgcaaggatt tcggagtctt gatgaaggag aacgtgtatc   300
atactacatt caagagcgat cgaatggaaa aggtagagaa gcttatgcgg tatcaggaga   360
agtagaagga caaggactga aggaagccg aattcatcca ttgggtcgta agaaggctgt    420
ctcactacgt tgcttcagat gtggaaagtt tgcgactcac aaggcgaaaa gttgtccaaa   480
cgtaaaaacc gatgcaaaag tgtgttatac ctgtggatcc gaggagcacg tgagctcaat   540
ctgtcctgaa agacgacgaa agcatcgacc ggaacaagtt gccgcagagg aagcagaagc   600
tgcgagaatg gcagctgaaa atcatcacc gactacatct gacgatgata ttagagaaaa    660
gaatagtaat tcctctgatg aatagaatca tctagacact gagaatattg atagagaaat   720
aatggaatat atggtctcaa atagattttg tctcgaaatt cttgaacatc caaatttaaa   780
tgtgaaaatt ttaggaaata attttgagct ttctgatagt ttttcagctt ttgaaatgta   840 ttttatttg aaaccaatat ttatttcatt ttctgtctca tctaattctc agtttgcatg    900
cgttacttta acttacacac taactctttt tttattcaaa ttttgatgtt ttttttcaa    960 ttgtttact caaatttccc ctctaaacca tactaccacc tacctcctca aattgcactc   1020
tcagggattc ttttttttttt caaatagaac tgattgcacc tgttttcagg atctataaat 1080
cttataatat atttaacttt cgtgtctttt catgttcatg tatttcttgc tgaaatccat  1140
cattttctct gaaatctct actcgtaagt tccgctattg cgggcgaacg ctgaaataaa   1200
tcgagagttt tg                                                     1212

<210> SEQ ID NO 9
<211> LENGTH: 227
<212> TYPE: PRT
<213> ORGANISM: Caenorhabditis elegans

<400> SEQUENCE: 9

Met Ser Thr Val Val Ser Glu Gly Arg Asn Asp Gly Asn Asn Arg Tyr
1               5                   10                  15

Ser Pro Gln Asp Glu Val Glu Asp Arg Leu Pro Asp Val Val Asp Asn
            20                  25                  30

Arg Leu Thr Glu Asn Met Arg Val Pro Ser Phe Glu Arg Leu Pro Ser
        35                  40                  45

Pro Thr Pro Arg Tyr Phe Gly Ser Cys Lys Trp Phe Asn Val Ser Lys
    50                  55                  60

Gly Tyr Gly Phe Val Ile Asp Asp Ile Thr Gly Glu Asp Leu Phe Val
65                  70                  75                  80

His Gln Ser Asn Leu Asn Met Gln Gly Phe Arg Ser Leu Asp Glu Gly
            85                  90                  95
```

```
Glu Arg Val Ser Tyr Tyr Ile Gln Glu Arg Ser Asn Gly Lys Gly Arg
                100                 105                 110
Glu Ala Tyr Ala Val Ser Gly Glu Val Glu Gly Gln Gly Leu Lys Gly
            115                 120                 125
Ser Arg Ile His Pro Leu Gly Arg Lys Lys Ala Val Ser Leu Arg Cys
        130                 135                 140
Phe Arg Cys Gly Lys Phe Ala Thr His Lys Ala Lys Ser Cys Pro Asn
145                 150                 155                 160
Val Lys Thr Asp Ala Lys Val Cys Tyr Thr Cys Gly Ser Glu Glu His
                165                 170                 175
Val Ser Ser Ile Cys Pro Glu Arg Arg Lys His Arg Pro Glu Gln
            180                 185                 190
Val Ala Ala Glu Glu Ala Glu Ala Ala Arg Met Ala Ala Glu Lys Ser
        195                 200                 205
Ser Pro Thr Thr Ser Asp Asp Asp Ile Arg Glu Lys Asn Ser Asn Ser
210                 215                 220
Ser Asp Glu
225

<210> SEQ ID NO 10
<211> LENGTH: 2039
<212> TYPE: DNA
<213> ORGANISM: Caenorhabditis elegans

<400> SEQUENCE: 10
aacgtggcac catcagccaa atggagccag ccgggcactc aagcgcaaca cataacatcg      60
ttgtgcccaa cgccaatccc acgcagcccc aaccacttgc accagcaatg cgtgaggaag     120
gtgccacgtt gtcaccccg aacacctggt cctcgtcctc cgtagaattt ctggacgacg     180
cggacgacaa tcgactcttg ttcacgtgca ccttcacatt ccccacggt accgtactct     240 catctgccac gtatgctgac ggattccacg agcaatattt gacgattgga gataactttc     300
tggcgaggct agagcccaag ggacagagct tcatcttgtc cgccgccgcc gcttcggtaa     360
agcagaggat ttttgcaagg gttactatgc agacggagc cctgcgggcc tgtgagctgc     420
tttgcgagtt cgagaccgat cgggccaaga tcaccgtgtt ggcgttgcga tcggcgttca     480
gtcttcaggc cagccacgtg tcatccaact ccacgtctt cactttcatc accaagcact     540
cgtcgacgtg tgctcttacc catattgatt acgcctcgat tccataccct ggtctcctac     600
ccaccgatct cattggtaaa tcactgctag ccttttgtcta ttccccagat gtacatgtcg     660
tgcggcaggc gcacattgat cttcacaact cgcgcggaaa gatcgtcaaa tccatcgccg     720
acctccgact cgtcgcccac aacggatcga tcctccgatg ccagaccgaa tggagcgcct     780
acgtgaatcc atggacccga aaaatggagc tagtcgtcgc cagacaccgt atctgctccc     840
ttccaatcgg agactcggat gtgatctcct caccaccacc aggcatccag tcaaacaccc     900
tgccaccggt tatggcgaag actttcgagg atgagctgag aactattatg aataagccag     960
taccatccac ctcccgtcac agccaccacc accatcactc aagcctcaag gatcagaacc    1020
agggcttccc ggccaacatc gacctgggcg cctacatcga caaaattgtc gagcaactcg    1080
ttgtcaactc cacagcccag caacagcaga aggtagccgt cgccgccgcc gcagccgctc    1140
aggcagccca ggccgccgta gtcgccaccg cccagatcag gaagttgcc agcgccccgc    1200 cgaccacctc aacggaccca ccactcagct acacacagat taactgtctg gagaatgtgc    1260
acaggttgtt gaagtctcag agtaggccgg aaagcccagc gaaacaagat gagccgttcg    1320
atgagaagaa gtacccaccg cagacgccac tgacccgaga agcactgaca ctgcacacca    1380
```

```
agcgatttga agacgagtac aaggacactt ggtgcagacg cctgaaacgc ctatccgacg    1440
atgtcccgag ctccccacca gcgaagcgta cgacgccgat ccactggaca tcctcctcgc    1500
agaaccatta ccggacaatg gcacccgccc caccaccgcc accgggcaag aactatcaga    1560
tcacctacac tccactggac gacctgaccg accaaaagtc caccaacacc aagtccgacg    1620
tggaaaacgt ggcctatcca atctcgggct ccaagttctc cacccaatg cggctctcga     1680 ttgacgggct tctgccacgt ggtgctacgt cgactggcgg tgcttccacg acaagtggca    1740
ccaactcgcc gcccgtcttc ccgaaaactt cctcatcctc ctctctccta atgctacggg    1800
attctcagaa ttaataagct actgcccaat ttttctttca attttaatt tttttcgaat     1860 tttgagtcga aatttgagtt cagtgcgctc agagcttttg aatgagtacc cacaagccta    1920
taggcctata tgggcctgaa cccggcctga acgggcattg aaaagcctga aaagcctga     1980 aaagcctaga caataatgtt tttctacatg actcctcgga agttttgata taaaatcca    2039
```

<210> SEQ ID NO 11
<211> LENGTH: 597
<212> TYPE: PRT
<213> ORGANISM: Caenorhabditis elegans

<400> SEQUENCE: 11

```
Met Glu Pro Ala Gly His Ser Ser Ala Thr His Asn Ile Val Val Pro
1               5                   10                  15

Asn Ala Asn Pro Thr Gln Pro Gln Pro Leu Ala Pro Ala Met Arg Glu
            20                  25                  30

Glu Gly Ala Thr Leu Ser Pro Pro Asn Thr Trp Ser Ser Ser Ser Val
        35                  40                  45

Glu Phe Leu Asp Asp Ala Asp Asp Asn Arg Leu Leu Phe Thr Cys Thr
    50                  55                  60

Phe Thr Leu Pro His Gly Thr Val Leu Ser Ala Thr Tyr Ala Asp
65                  70                  75                  80

Gly Phe His Glu Gln Tyr Leu Thr Ile Gly Asp Asn Phe Leu Ala Arg
                85                  90                  95

Leu Glu Pro Lys Gly Gln Ser Phe Ile Leu Ser Ala Ala Ala Ala Ser
            100                 105                 110

Val Lys Gln Arg Ile Phe Ala Arg Val Thr Met Pro Asp Gly Ala Leu
        115                 120                 125

Arg Ala Cys Glu Leu Leu Cys Glu Phe Glu Thr Asp Arg Ala Lys Ile
    130                 135                 140

Thr Val Leu Ala Leu Arg Ser Ala Phe Ser Leu Gln Ala Ser His Val
145                 150                 155                 160

Ser Ser Asn Phe His Val Phe Thr Phe Ile Thr Lys His Ser Ser Thr
                165                 170                 175

Cys Ala Leu Thr His Ile Asp Tyr Ala Ser Ile Pro Tyr Leu Gly Leu
            180                 185                 190

Leu Pro Thr Asp Leu Ile Gly Lys Ser Leu Leu Ala Phe Val Tyr Ser
        195                 200                 205

Pro Asp Val His Val Val Arg Gln Ala His Ile Asp Leu His Asn Ser
    210                 215                 220

Arg Gly Lys Ile Val Lys Ser Ile Ala Asp Leu Arg Leu Val Ala His
225                 230                 235                 240

Asn Gly Ser Ile Leu Arg Cys Gln Thr Glu Trp Ser Ala Tyr Val Asn
                245                 250                 255

Pro Trp Thr Arg Lys Met Glu Leu Val Val Ala Arg His Arg Ile Cys
```

```
                    260                 265                 270
Ser Leu Pro Ile Gly Asp Ser Asp Val Ile Ser Pro Pro Gly
        275                 280                 285

Ile Gln Ser Asn Thr Leu Pro Pro Val Met Ala Lys Thr Phe Glu Asp
        290                 295                 300

Glu Leu Arg Thr Ile Met Asn Lys Pro Val Pro Ser Thr Ser Arg His
305                 310                 315                 320

Ser His His His His Ser Ser Leu Lys Asp Gln Asn Gln Gly Phe
                325                 330                 335

Pro Ala Asn Ile Asp Leu Gly Ala Tyr Ile Asp Lys Ile Val Glu Gln
            340                 345                 350

Leu Val Val Asn Ser Thr Ala Gln Gln Gln Gln Lys Val Ala Val Ala
                355                 360                 365

Ala Ala Ala Ala Ala Gln Ala Ala Gln Ala Ala Val Val Ala Thr Ala
        370                 375                 380

Gln Ile Arg Lys Val Ala Ser Ala Pro Pro Thr Thr Ser Thr Asp Pro
385                 390                 395                 400

Pro Leu Ser Tyr Thr Gln Ile Asn Cys Leu Glu Asn Val His Arg Leu
                405                 410                 415

Leu Lys Ser Gln Ser Arg Pro Glu Ser Pro Ala Lys Gln Asp Glu Pro
            420                 425                 430

Phe Asp Glu Lys Lys Tyr Pro Pro Gln Thr Pro Leu Thr Arg Glu Ala
                435                 440                 445

Leu Thr Leu His Thr Lys Arg Phe Glu Asp Glu Tyr Lys Asp Thr Trp
        450                 455                 460

Cys Arg Arg Leu Lys Arg Leu Ser Asp Asp Val Pro Ser Ser Pro Pro
465                 470                 475                 480

Ala Lys Arg Thr Thr Pro Ile His Trp Thr Ser Ser Gln Asn His
                485                 490                 495

Tyr Arg Thr Met Ala Pro Ala Pro Pro Pro Pro Gly Lys Asn Tyr
            500                 505                 510

Gln Ile Thr Tyr Thr Pro Leu Asp Asp Leu Thr Asp Gln Lys Ser Thr
                515                 520                 525

Asn Thr Lys Ser Asp Val Glu Asn Val Ala Tyr Pro Ile Ser Gly Ser
        530                 535                 540

Lys Phe Ser Thr Pro Met Arg Leu Ser Ile Asp Gly Leu Leu Pro Arg
545                 550                 555                 560

Gly Ala Thr Ser Thr Gly Gly Ala Ser Pro Thr Ser Gly Thr Asn Ser
                565                 570                 575

Pro Pro Val Phe Pro Lys Thr Ser Ser Ser Ser Leu Leu Met Leu
            580                 585                 590

Arg Asp Ser Gln Asn
        595

<210> SEQ ID NO 12
<211> LENGTH: 21
<212> TYPE: DNA
<213> ORGANISM: Caenorhabditis elegans

<400> SEQUENCE: 12
tccctgagac ctcaagtgtg a                                              21

<210> SEQ ID NO 13
<211> LENGTH: 22
<212> TYPE: DNA
<213> ORGANISM: Caenorhabditis elegans
```

```
<400> SEQUENCE: 13
tccctgagac cctaacttgt ga                                              22

<210> SEQ ID NO 14
<211> LENGTH: 24
<212> TYPE: DNA
<213> ORGANISM: Caenorhabditis elegans

<400> SEQUENCE: 14
tccctgagaa ttctcgaaca gctt                                            24

<210> SEQ ID NO 15
<211> LENGTH: 22
<212> TYPE: DNA
<213> ORGANISM: Caenorhabditis elegans

<400> SEQUENCE: 15
tccctgagac ctttaacctg tg                                              22
```

ANTI-AGING MICRORNAS

CROSS-REFERENCE TO RELATED APPLICATIONS

This application claims priority to U.S. Ser. No. 60/693,395 filed Jun. 23, 2005 entitled "MicroRNAs Combat Diseases of Aging" by Frank J. Slack and Michelle M. Boehm.

STATEMENT REGARDING FEDERALLY FUNDED RESEARCH

The Federal Government has certain rights in this invention by virtue of Grant No. GM647701 from the National Institute of Health to Frank J. Slack and Grant No. DO1119 from the National Science Foundation to Frank J Slack.

BACKGROUND

Age-related disorders including Alzheimer's disease affect an estimated 4.5 mlllion Americans. National direct and indirect annual costs of caring for individuals with Alzheimer's disease are at least $100 billion, according to estimates used by the Alzheimer's Association and the National Institute on Aging. Parkinson's disease affects over 1 million people in the US alone and is one of the most common debilitating diseases in the country. According to the National Parkinson's Foundation, each individual spends an average of $2,500 a year for medications. Estimates of costs of medical care, disability payments and lost income exceed $5.6 billion annually. Thus, age-related disorders have a significant impact and understanding the aging process may help develop new therapies for these and other disorders.

Multiple contributions to aging and lifespan regulation in animals have been proposed, including accumulation of oxidatively damaged macromolecules, shortened telomeres, progeny production, metabolic rate, caloric intake, and the existence of an aging program that acts as a timing mechanism (Tissenbaum, H. A. and L. Guarente, (2002) Dev Cell, 2(1), 9-19). The ease of genetic analysis and modest life span of *Caenorhabditis elegans* (*C. elegans*) has made it the multicellular organism of choice for the investigation into the genetic basis of aging and longevity.

The *C. elegans* insulin/IGF-1-like signaling pathway is the best-characterized pathway modulating aging, and single gene mutations in this pathway have been shown to significantly affect lifespan. For example, loss of function (lf) mutations in daf-2, the insulin/IGF-1 receptor homolog, cause the animal to live twice as long as wild-type animals (Kenyon, C., et al., (1993) Nature, 366(6454), 461-4). Many molecular studies have shown that DAF-2 activates a phosphatidylinositol-3-OH (PI3K) signaling cascade, which ultimately acts to antagonize the DAF-16 forkhead family transcription factor. DAF-16 is then unable to repress genes that regulate longevity, as well as the dauer diapause decision and stress response, and to activate genes that are required for metabolism and reproductive growth.

While many factors that regulate aging in *C. elegans* have been identified, it is apparent that the global genetic patterns required for lifespan determination have not yet been completely defined. Changes in gene expression in aged adults across species do not solely seem to be implemented in response to mounting damage; rather, conserved, developmentally timed transcriptional regulation during young adulthood seems to control features of aging (McCarroll, S. A., et al. (2004) Nat Genet, 36(2), 197-204). For example, young adult *C. elegans* and *Drosophila* animals turn off a conserved battery of oxidative respiration genes and turn on stress response genes. A similar trend is seen in human brain tissue, where the switch occurs at around age 40 (Lu, T., et al., (2004) Nature, 429(6994), 883-91). This implies that aging, or more specifically the time of death, is under temporal control at the genetic level.

It is an object of the present invention to provide genes involved in senescence, aging or age-related disorders which can be used as drug targets or in drug design for compounds decreasing one or more characteristics of aging.

It is another object of the present invention to provide inhibitory compositions, including nucleic acid molecules such as miRNAs, for inhibition of expression of one or more genes involved in senescence, aging, or age-related disorders.

It is further an object of the present invention to provide nucleic acids for diagnosis, treatment or prophylaxis of one or more symptoms of senescence, aging, or age-related disorders.

BRIEF SUMMARY OF THE INVENTION

Methods and compositions for modulating aging genes or their targets for the treatment or prevention of senescence or symptoms thereof have been developed based on the discovery of naturally occurring inhibitory nucleic acids, in particular lin-4 miRNA, that downregulate genes involved in senescence, lifespan, or age-related disorders. Representative aging genes include, but are not limited to lin-4, lin-14, let-7, lin-28, egl-35 and lin-42. Methods for identifying modulators of aging genes and targets of aging genes are also provided.

The disclosed compositions are useful as diagnostics. These can be used in assays to compare genes in normal individuals, with those who are aging well or who demonstrate early senescence, and with those who have age-related disorders such as Parkinson's and Alzheimer's. In another embodiment, the genes are used to study the pathways and mechanisms involved in aging and age-related disorders.

These genes can be used as drug targets, or in drug design, to develop drugs that can inhibit one or more characteristics of senescence or age-related disorders. In one preferred embodiment, the genes are used for screening for compositions up-regulating certain aging genes, for example, lin-4 microRNAs or homologues thereof. These may be nucleic acid molecules, or compounds identified by screening of large libraries of small molecules, a number of which are commercially available. In other embodiments, compositions and methods for downregulating targets of lin-4 or homologues thereof are provided.

These compositions should be effective therapies for treating or slowing the effects of one or more symptoms or characteristics of age-related disorders resulting from activation or over-expression of aging genes. The compositions can be administered to an individual in need of treatment or prophylaxis of at least one symptom or manifestation (since disease can occur/progress in the absence of symptoms) of an age-related disorder, or someone who is aging prematurely. In one embodiment, the compositions are administered in an effective amount to inhibit expression of lin-4 age-regulating targets like lin-14. In another embodiment, the compositions are administered in an amount effective to enhance or increase expression of lin-4. In a more preferred embodiment, the compositions are administered in an effective amount to alter the insulin-like signal pathway. Effective, safe dosages can be experimentally determined in model organisms and in human trials by methods well known to one of ordinary skill in the art. The compositions can be administered alone or in combination with a second therapeutic for the treatment of age-related disorders to improve at least one symptom or manifestation of age-related disease.

Representative compounds and compositions include, but are not limited to inhibitory nucleic acids such as miRNA, antibodies and antigen binding fragments thereof, and small molecule inhibitors or activators. MiRNA nucleic acids including pri-miRNA, pre-miRNA, mature MiRNA or fragments of variants thereof that retain the biological activity of mature miRNA and DNA encoding a pri-miRNA, pre-miRNA, mature miRNA, fragments of variants thereof, or regulatory elements of the miRNA, referred to jointly as "miRNAs" unless otherwise stated, are described. In one embodiment, the size range of the miRNA can be from 21 nucleotides to 170 nucleotides, although miRNAs of up to 2000 nucleotides can be utilized. In a preferred embodiment the size range of the miRNA is from 70 to 170 nucleotides in length. In another preferred embodiment, mature miRNAs of from 21 to 25 nucleotides in length can be used.

DETAILED DESCRIPTION

Definitions

Figure 1A:
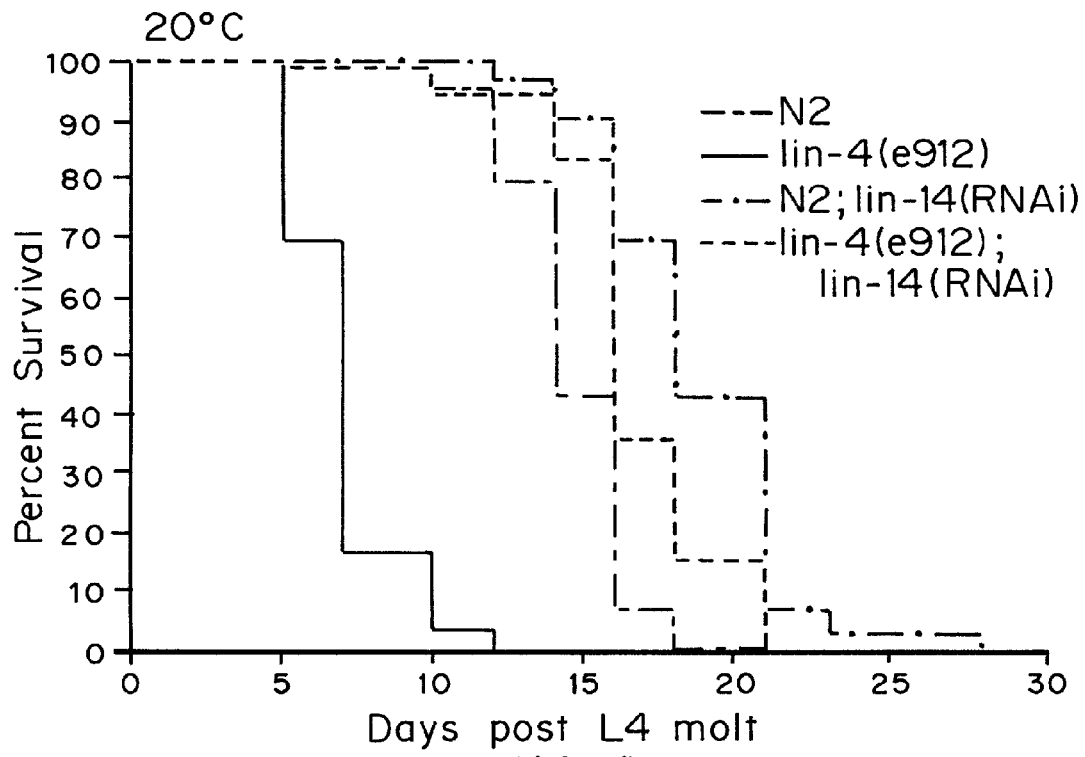
FIGS. 1A-D show line graphs of days versus percent survival for various lin-4 and lin-14 mutants.

As used herein the term "nucleic acid" refers to multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). The term shall also include polynucleosides (i.e. a polynucleotide minus the phosphate) and any other organic base containing polymer. Purines and pyrimidines include but are not limited to adenine, cytosine, guanine, thymidine, inosine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art. Thus, the term nucleic acid also encompasses nucleic acids with substitutions or modifications, such as in the bases and/or sugars.

The term "age-related disorder" refers to disorders associated with senescence, including for example, disorders characterized by, identifiable or associated with, altered expression of lin-4, lin-14, egl-35, lin-42, lin-28, let-7 or homologues thereof relative to normal age controls. Representative age-related disorders include, but are not limited to, Alzheimer's disease, Parkinson's disease, diabetes, atherosclerosis, osteoporosis, memory loss, arthritis, high blood pressure, stroke, aneurism, sarcopenia, progeria, wrinkles/skin blemishes/liver spots, obesity, cancer, pain, urinary incontinenece, locomotor dysfunction, sterility, sexual dysfunction, and dementia.

The term "inhibitory nucleic acid" refers to a nucleic acid specific for a target nucleic acid and inhibits the expression of the target nucleic acid. Representative inhibitory nucleic acids include, but are not limited to siRNA, miRNA, antisense RNA, DNA, or a combination thereof. Expression of the target nucleic acid can be inhibited at the transcriptional or translational level.

To "alter" the expression of a target gene or mRNA means that the level of expression of the target gene or mRNA after applying a method of the present invention is different from its expression before applying the method. For example, lin-4, lin-14, mir-125a, or mir-125b or any protein or nucleic acid encoded by these genes or other genes disclosed herein can be altered by application of any of the disclosed methods or compositions. To alter gene expression includes reducing the expression of the target gene, for example the expression of the gene or mRNA is not detectable. To alter gene expression also includes increasing expression of the target gene or overexpressing the target gene compared to its expression before applying the method. The alteration of the expression of the target gene may result in a knockout mutant phenotype.

The term "orthologues" refers to separate occurrences of the same gene in multiple species. The separate occurrences have similar, albeit nonidentical, amino acid sequences, the degree of sequence similarity depending, in part, upon the evolutionary distance of the species from a common ancestor having the same gene.

As used herein, the term "paralogues" indicates separate occurrences of a gene in one species. The separate occurrences have similar, albeit nonidentical, amino acid sequences, the degree of sequence similarity depending, in part, upon the evolutionary distance from the gene duplication event giving rise to the separate occurrences.

As used herein, the term "homologues" is generic to "orthologues" and "paralogues".

As used herein, the term "microRNA" refers to any type of interfering RNA, including but not limited to, endogenous microRNA and artificial microRNA. Endogenous microRNAs are small RNAs naturally present in the genome which are capable of modulating the productive utilization of mRNA. The term artificial microRNA includes any type of RNA sequence, other than endogenous microRNA, which is capable of modulating the productive utilization of mRNA.

"MicroRNA flanking sequence" as used herein refers to nucleotide sequences including microRNA processing elements. MicroRNA processing elements are the minimal nucleic acid sequences which contribute to the production of mature microRNA from precursor microRNA. Precursor miRNA termed pri-miRNAs are processed in the nucleus into about 70 nucleotide pre-miRNAs, which fold into imperfect stem-loop structures.

The microRNA flanking sequences may be native microRNA flanking sequences or artificial microRNA flanking sequences. A native microNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. The artificial microRNA flanking sequences may be flanking sequences found naturally in the context of other microRNA sequences. Alternatively they may be composed of minimal microRNA processing elements which are found within naturally occurring flanking sequences and inserted into other random nucleic acid sequences that do not naturally occur as flanking sequences or only partially occur as natural flanking sequences.

The microRNA flanking sequences within the precursor microRNA molecule may flank one or both sides of the stem-loop structure encompassing the microRNA sequence. Preferred structures have flanking sequences on both ends of the stem-loop structure. The flanking sequences may be directly adjacent to one or both ends of the stem-loop structure or may be connected to the stem-loop structure through a linker, additional nucleotides or other molecules.

As used herein a "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures and terms are well known in the art. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base-pairing may not include any mismatches.

Small RNA molecules are single stranded or double-stranded RNA molecules generally less than 200 nucleotides in length. Such molecules are generally less than 100 nucleotides and usually vary from 10to 100 nucleotides in length. In a preferred format, small RNA molecules have 11, 12, 13, 14, 15, 16, 17, 18, 19, 20, 21, 22, 23, 24, 25, 26, 27, 28, 29, or 30 nucleotides. Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded.

The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription produce of siRNA to be expressed can be, for example, 15 to 49 bp, preferably 15 to 35 bp, and more preferably 21 to 30 bp long. The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. Nonpairing portions can be contained to the extent that they do not interfere with siRNA formation. The "bulge" used herein preferably comprise 1 to 2 nonpairing nucleotides, and the double-stranded RNA region of siRNAs in which two strands pair up contains preferably 1 to 7, more preferably 1 to 5 bulges. In addition, the "mismatch" as used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have at low molecular weight RNA. As described above, this low molecular weight RNA may be a natural RNA molecule such as tRNA, rRNA or viral RNA, or an artificial RNA molecule.

"Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form siRNA. These antisense and sense RNAs have been conventionally synthesized with an RNA synthesizer. In the present invention, these RNAs can be intracellularly expressed from DNAs coding for antisense and sense RNAs (antisense and sense code DNAs) respectively using the siRNA system.

As used herein, the term "lin-4" refers to the nucleic acid encoding the lin-4 miRNA and homologues and variants thereof including conservative substitutions, additions, and deletions therein not adversely affecting the structure or function. Preferably, lin-4 refers to the nucleic acid encoding lin-4 from *C. elegans* (NCBI Accession No. NM_077516 most preferably, lin-4 refers to the nucleic acid encoding a lin-4 family member from humans, including but not limited to miR-125a and miR-125b, miRBase Accession Nos. MI0000469, MI0000446, MI0000460, and biologically active sequence variants of lin-4, including alleles, and in vitro generated derivatives of lin-4 that demonstrate lin-4 activity, for example the down regulation of lin-4 target genes, e.g., lin-14 or homologues or variants thereof.

Sequence variants of lin-4 fall into one or more of three classes: substitutional, insertional or deletional variants. Insertions include 5' and/or 3' terminal fusions as well as intrasequence insertions of single or multiple residues. Insertions can also be introduced within the mature sequence of lin-4. These, however, ordinarily will be smaller insertions than those at the 5' or 3' terminus, on the order of 1 to 4 residues.

Insertional sequence variants of lin-4 are those in which one or more residues are introduced into a predetermined site in the target lin-4. Most commonly insertional variants are fusions of nucleic acids at the 5' or 3' terminus of lin-4.

Deletion variants are characterized by the removal of one or more residues from the lin-4 RNA sequence. These variants ordinarily are prepared by site specific mutagenesis of nucleotides in the DNA encoding lin-4, thereby producing DNA encoding the variant, and thereafter expressing the DNA in recombinant cell culture. However, variant lin-4 fragments may be conveniently prepared by in vitro synthesis. The variants typically exhibit the same qualitative biological activity as the naturally-occurring analogue, although variants also are selected in order to modify the characteristics of lin-4.

Substitutional variants are those in which at least one residue sequence has been removed and a different residue inserted in its place. While the site for introducing a sequence variation is predetermined, the mutation per se need not be predetermined. For example, in order to optimize the performance of a mutation at a given site, random mutagenesis may be conducted at the target region and the expressed lin-4 variants screened for the optimal combination of desired activity. Techniques for making substitution mutations at predetermined sites in DNA having a known sequence are well known.

Nucleotide substitutions are typically of single residues; insertions usually will be on the order of about from 1 to 10 residues; and deletions will range about from 1 to 30 residues. Deletions or insertions preferably are made in adjacent pairs; i.e., a deletion of 2 residues or insertion of 2 residues. Substitutions, deletion, insertions or any combination thereof may be combined to arrive at a final construct. Changes may be made to increase the activity of the miRNA, to increase its biological stability or half-life, and the like. All such modifications to the nucleotide sequences encoding such miRNA are encompassed.

A DNA isolate is understood to mean chemically synthesized DNA, cDNA or genomic DNA with or without the 3' and /or 5' flanking regions. DNA encoding lin-4 can be obtained from other sources by a) obtaining a cDNA library from cells containing mRNA, b) conducting hybridization analysis with labeled DNA encoding lin-4 or fragments thereof (usually, greater than 100 bp) in order to detect clones in the cDNA library containing homologous sequences, and c) analyzing the clones by restriction enzyme analysis and nucleic acid sequencing to identify full-length clones.

As used herein nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTN using default parameters) are generally available. Software for performing BLAST analyses is publicly available through the National Center of Biotechnology Information (www.ncbi.nlm.nih.gov).

Compositions

A. "Aging Genes"

It has been discovered that heterochronic genes regulate the timing of death during adulthood, and that certain of them regulate *C. elegans* lifespan. One embodiment provides methods and compositions for altering these temporal controls, for example using nucleic acids such as microRNAs.

lin-4 encodes a microRNA (miRNA), a short regulatory RNA that binds to complementary sequences in the 3' untranslated region (UTR) of target mRNAs, such as lin-14 to repress their translation. As shown in FIG. 1A, lin-4 mutants exhibited a short lifespan (about half of wild-type), while over-expression of lin-4 or loss of lin-14 extended lifespan (by about 30%). lin-14(lf) caused an extended lifespan (and suppressed the short lifespan of lin-4) even when it was removed only in the adult stage, similar to daf-2(lf). Therefore, these genes act at least partially in the adult to regulate lifespan and their effects are not merely due to post-embryonic developmental effects.

Figure 8:
FIG. 8 shows sequence comparison of lin-4, mir-125a, mir-125b, mir-237.

The founding members of the miRNA family, lineage defective-4 (lin-4) and lethal-7 (let-7), were identified through genetic analysis to control the timing of stage-appropriate cell division and differentiation in *C. elegans* (Lee, et al. Cell (1993) 75(5):843-854; Reinhart, B., et al., Nature (2000) 403: 901-906; Slack, F. and G. Ruvkun, Annu Rev Genet (1997) 31: 611-34; Banerjee, D. and F. Slack, Bioessays (2002) 24(2):119-29). let-7 and lin-4 control the timing of proliferation versus differentiation decisions. Some of these genes, like lin-4 and let-7, encode microRNAs (miRNAs) that are conserved in humans. FIG. 8 shows a sequence comparison of lin-4 t0 mir-125a and mir-125b. Mutations in the lin-4 and let-7 miRNAs result in inappropriate reiterations of the first larval stage (L1) and the fourth stage (L4) fates, respectively, and these defects lead to disruptions in cell cycle exit (Lee, et al. Cell (1993) 75(5):843-854; Reinhart, B., et al., Nature (2000) 403:901-906). For example, in wild-type animals, specialized skin cells, known as seam cells, divide with a stem cell pattern and terminally differentiate at the beginning of the adult stage. The seam cells fail to terminally differentiate in lin-4 and let-7 mutant animals, and instead reiterate the larval fate and divide again. Lack of cell cycle control and failure to terminally differentiate are hallmarks of cancer.

The expression patterns for lin-4 and let-7 correlate with their role in directing developmental timing. lin-4 RNA accumulates during the L1 stage and is responsible for the L1/L2 transition in nematodes by inhibiting the expression of lin-14 and lin-28, repressors of post-L1 fates (Lee, et al. Cell (1993) 75(5):843-854; Ambros, V. and H. R. Horvitz, Science (1984) 226:409-416; Wightman, et al. Cell (1993) 75(5):855-862; Moss, et al. Cell (1997) 88(5): 37-46; and Feinbaum, R. and V. Ambros, Dev Biol (1999) 210(1):87-95). let-7 RNA accumulates during the L4 stage and is responsible for the L4/Adult transition by down-regulating the expression of lin-41, hbl-1 RAS (Johnson et al., Cell (2005) 120(5):635-47; Grosshans, et al., Dev Cell (2005) 8(3) 321-30; Lin, et al., Dev Cell (2003) 4(5):639-50; Slack, F. J., Molec. Cell (2000) 5:659-669).

These 21-22 nucleotide miRNAs exert their effect by binding to imperfect complementary sites within the 3'-untranslated regions (3'UTRs) of their target protein-coding mRNAs and repress the expression of these genes at the level of translation (Lee, et al. Cell (1993) 75(5):843-854; Reinhart, B., et al., Nature (2000) 403:901-906; Moss, et al. Cell (1997) 88(5):637-46; Lin, S. Y., et al., Dev Cell (2003) 4(5):639-50, Slack, F. J., et al., Molec. Cell (2000) 5:659-669); Abrahante, J. E., et al., Dev Cell (2003) 4(5):625-37; and Olsen, P. H. and V. Ambros, Dev Biol (1999) 216(2):671-80).

The lin-4 miRNA is a well-characterized temporal identity gene that directs the fate choices that cells make at specific times during larval development of C. elegans by down regulation of its targets, like the transcription factor lin-14 and lin-28. lin-4 mutants consistently aged prematurely as judged by precocious expression of the gut autofluorescene marker. In addition, the premature gut autofluorescence expression of phenotype of lin-4 mutants could be suppressed by mutations in lin-14, while lin-14 mutants displayed a delayed expression of the gut autofluorescence marker.

Stress sensitivity has been shown to positively correlate with lifespan in several species, including C. elegans, Drosophila, and rats. In accordance with their lifespan phenotypes, lin-4 lf mutants were stress-sensitive while lin-14 lf mutants were stress-resistant as compared to wild-type. Finally, the perturbation in longevity due to lin-4 and lin-14 mutation was not merely due to developmental abnormalities. This indicated that these genes function in the adult to regulate lifespan. Moreover, lin-14 represses a molecule in the insulin-like signaling pathway, a pathway known to regulate lifespan in nematodes, flies, and mice. Therefore, altering expression of these specific microRNAs or homologues thereof, or providing analogous agonist or antagonist pharmaceutical compounds exogenously, should be effective therapies for insulin/IGF-1-like signaling pathway mediate disorders and age-related disorders resulting from activation or over or under-expression of lin-4, lin-14, or homologues thereof.

lin-4 miRNA is evolutionarily conserved in higher animals, including humans and temporally expressed which implies a universal role for this miRNA during animal development (Lagos-Quintana, M., et al., Mouse, Curr Biol (2002) 12(9):735-9 and Pasquinelli, A. E., et al., Nature (2000) 408 (6808):86-9). There are 2 human and mouse homologues of lin-4, named mir-125a and mir-125b. Therefore, lin-4 miRNA, mir-125a and mir-125b should be effective in several species to alter the insulin or insulin-like signaling pathway, in particular to downregulate lin-4 targets like lin-14 or homologues thereof.

B. Modulators of lin-14 Targets such as lin-14 or Homologues Thereof

Nucleic Acid Modulators

Certain embodiments provide microRNA compositions and methods of their use in the treatment, prevention or diagnosis of age-related disorders or premature aging. Micro RNAs (referred to as "miRNAs") are small non-coding RNAs, belonging to a class of regulatory molecules found in plants and animals that control gene expression by binding to complementary sites on target messenger RNA (mRNA) transcripts. miRNAs are generated from large RNA precursors (termed pri-miRNAs) that are processed in the nucleus into approximately 70 nucleotide pre-miRNAs, which fold into imperfect stem-loop structures (Lee, Y., et al., Nature (2003) 425(6956):415-9). The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science (2001) 12:12 and Grishok, A., et al., Cell (2001) 106(1):23-34). MiRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the ribonucleoprotein complex known as the RISC complex. This mechanism of miRNA-mediated gene silencing has been observed mainly in plants (Hamilton, A. J. and D. C. Baulcombe, Science (1999) 286 (5441):950-2 and Reinhart, B. J., et al., *MicronRNAs in plants*, Genes and Dev. (2002) 16:1616-1626), but an example is known from animals (Yekta, S., I. H. Shih, and D. P. Bartel, Science (2004) 304(5670):594-6). In the second mechanism, miRNAs that bind to imperfect complementary sites on messenger RNA transcripts direct gene regulation at the posttranscriptional level but do not cleave their mRNA targets. MiRNAs identified in both plants and animals use this mechanism to exert translational control of their gene targets (Bartel, D. P., Cell (2004) 116(2):281-97).

In preferred embodiments, one or more inhibitory nucleic acids specific for lin-4 targets such as lin-14 or homologues thereof are administered to individuals having an age-related disorder or symptom thereof. More preferably, the formulations are administered to individuals to reduce or inhibit expression or function of target genes like lin-14 expression or function. The inhibitory nucleic acid can be siRNA, miRNA, antisense RNA, or antisense DNA. Typically, the inhibitory nucleic acid comprises lin-4 miRNA or variants thereof. In certain embodiments, the inhibitory nucleic acid has at least 80%, typically at least 90%, even more typically at least 95% sequence identity with lin-4 miRNA. It will be appreciated that the inhibitory nucleic acid can include RNA or DNA components as well as artificial nucleotides and artificial nucleoside linkages. Other embodiments provide administering modulators of lin-4 that enhance or increase expression of lin-4 in the individual or a cell of the individual. One embodiment provides an inhibitory nucleic acid that has at least 80%, typically at least 90%, even more typically at least 95% sequence identity with mir-125a or mir-125b miRNA.

Naturally occurring microRNAs that regulate lin-14 or homologues thereof, pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA, have been identified. The size of the miRNA is typically from 21 nucleotides to 170 nucleotides, although nucleotides of up to 2000 nucleotides can be utilized. In a preferred embodiment the size range of the pre-miRNA is between 70 to 170 nucleotides in length and the mature miRNA is between 21 and 25 nucleotides in length. One embodiment provides an miRNA that has at least 80% sequence identity with lin-4, mir-125a, or mir-125b. The sequence data for lin-4l, mir-125a, and mir-125b are known in the art and the accession numbers are provided below.

|  | SEQ ID NO | Accession No. |
| --- | --- | --- |
| lin-4 miRNA | SEQ ID NO: 1 | AY390761 |
| Lin-4 gene | SEQ ID NO: 2 | U01830 |
| lin-14 gene | SEQ ID NO: 3 | NM_077516 |
| LIN-14 protein | SEQ ID NO: 4 | NM_077516 |
| mir-125a miRNA | SEQ ID NO: 5 | MI0000469 |
| mir-125b miRNA | SEQ ID NO: 6 | MI0000446 |
| let-7 miRNA | SEQ ID NO: 7 | AY390762 |
| lin-28 gene | SEQ ID NO: 8 | NM_001025914 |
| lin-28 protein | SEQ ID NO: 9 | NM_001025914 |
| lin-42 gene | SEQ ID NO: 10 | NM_001027006 |
| lin-42 protein | SEQ ID NO: 11 | NM_001027006 |

Small Molecule Modulators

Modulators of lin-14, lin-4, mir-125a, mir-125b, egl-35, lin-28, lin-42, and let-7 can be identified by screening combinatorial libraries and databases. Modulators can be identified using routine screening based on the discovery of the role of lin-14. As used herein the term "test compound" or "modulator" refers to any molecule that may potentially inhibit or enhance lin-14 or lin-4 (or other genes discussed herein) expression or function. Some test compounds and modulators can be compounds that are structurally related to LIN-14, EGL-35 or LIN-42 polypeptides. Compounds can be identified by selecting for a compound that promotes or interferes with lin-14 or lin-4 mediated insulin-like signaling pathway or modulates lifespan compared to a control compound. Typically, compounds that increase lifespan or cell survivability are selected. In certain embodiments, the cell can be obtained from biologic samples, for example from an individual in which one or more aging genes have altered expression or activity.

Small molecule libraries that are believed to meet the basic criteria for useful drugs can be screened to identify useful compounds. Screening of such libraries, including combinatorially generated libraries (e.g., expression libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

In one screening method, increasing survivability of a cell contacted with a compound such as a nucleic acid that binds and inhibits expression of aging genes like lin-14 in an amount effective to alter insulin-like signaling is used to identify a modulator. The survivability of the cell can be compared to survivability of a cell that is not contacted with the molecule. Representative inhibitory nucleic acids include, but are not limited to lin-4 miRNA, mi-125a, mi-125b variants and homologues thereof.

Modulators of lin-14, lin-4, mir-125a, mir-125b, egl-35, lin-28, lin-42, and let-7 can also be identified by review of the nucleic acid sequences and three dimensional structure of the genes, and mutational analysis, using standard computer aided drug design to make compounds which mimic the activity of the genes or proteins encoded thereby, or which inhibit the activity of the genes or proteins encoded thereby. One embodiment provides small molecule analogues of lin-4, nir-125a, mir-125b, and homologues thereof. In other embodiments, the small molecules are antagonists of lin-14 and homologues thereof. Small molecules that inhibit lin-42, egl-35 or lin-14 expression or function or upregulate let-7, lin-4, mir-125a, or mir-125b expression or function can be designed entirely de novo or may be based upon a pre-existing regulators of the respective target. Either of these approaches can be facilitated by screening databases and libraries of small molecules for chemical entities, agents, ligands, or compounds that can bind in whole, or in part, to lin-14 or lin-4 nucleic acid or protein or homologues thereof. In this screening, the quality of fit of such entities or compounds to the binding site or sites may be judged either by shape complementarity or by estimated interaction energy (Meng et al., (1992) J. Comp. Chem. 13: 505-524).

The design of molecules that bind to or inhibit the functional activity of genes like lin-14 or homologues thereof or that upregulate or enhance the expression or function of lin-4 and homologues thereof generally involves consideration of two factors. First, the molecule must be capable of physically and structurally associating with target nucleic acid or protein or a regulator or the target nucleic acid or protein. Non-covalent molecular interactions important in the association of nucleic acids with the molecule, include hydrogen bonding, van der Waals and hydrophobic interactions. Second, the molecule must be able to assume a conformation that allows it to associate with the target nucleic acid or protein. Although certain portions of the molecule may not directly participate in this association with the target nucleic acid or protein those portions may still influence the overall conformation of the molecule. This, in turn, may have a significant impact on binding affinities, therapeutic efficacy, drug-like qualities, and potency. Such conformational requirements include the overall three-dimensional structure and orientation of the chemical entity or molecule in relation to all or a portion of the active site or other region of the nucleic acid or protein, or the spacing between functional groups of a molecule comprising several chemical entities that directly interact with the target nucleic acid or protein.

The potential, predicted, inhibitory or binding effect of a molecule on the target nucleic acid or protein may be analyzed prior to its actual synthesis and testing by the use of computer modeling techniques. If the theoretical structure of the given molecule suggest insufficient interaction and association between it and the target nucleic acid or protein, synthesis and testing of the molecule is obviated. However, if computer modeling indicates a strong interaction, the molecule may then be synthesized and tested for its ability to interact with the target nucleic acid or protein and inhibit lin-14 expression or function or enhance lin-4 expression or function. In this manner, synthesis of inoperative molecules may be avoided. In some cases, inactive molecules are synthesized predicted on modeling and then tested to develop a structure-activity relationship for molecules interacting with a specific region of the target nucleic acid or protein.

One skilled in the art may use one of several methods to identify chemical moieties or entities, compounds, or other agents for their ability to associate with a target nucleic acid, for example, associate with the nucleic acid or protein of lin-4, lin-14, mir-125a, mir-125b, or homologues thereof. This process may begin by visual inspection or computer assisted modeling of, for example, the target site on the computer screen based on the atomic co-ordinates of the lin-14 nucleic acid or protein complexes with other analogues. In one embodiment, compound design uses computer modeling programs which calculate how different molecules interact with the various sites of the lin-4, lin-14, mir-125a, mir-125b nucleic acid, protein, or a fragment thereof. Selected chemical moieties or entities, compounds, or agents may then be positioned in a variety of orientations within at least a portion of the target nucleic acid or protein.

The modulators can be small molecules, typically synthetic molecules, usually organic molecules, nucleic acids such as catalytic nucleic acids such as DNAzymes and ribozymes, external guide sequences for ribonuclease P, siRNA, microRNA, anti-sense RNA, anti-sense DNA, or polypeptides, such as antibodies and antigen binding fragments thereof. The modulators can interact directly with the target nucleic acid or protein, or can act upstream of insulin-signaling pathway to modulate expression of the target. Test compounds may include fragments or parts of naturally-occurring compounds, or may be found as active combinations of known compounds, which are otherwise inactive. Compounds isolated from natural sources, such as animals, bacteria, fungi, plant sources, including leaves and bark, and marine samples can be assayed as candidates for the presence of potentially useful pharmaceutical agents. It will be understood that the pharmaceutical agents to be screened could also be derived or synthesized from chemical compositions or man-made compounds. Thus, it is understood that the test compound identified by embodiments of the present disclosure may be peptide, polypeptide, polynucleotide, small molecule inhibitors, small molecule inducers, organic or inorganic, or any other compounds that may be designed based on known inhibitors or stimulators.

In addition to the modulating compounds initially identified, other sterically similar compounds may be formulated to mimic the key portions of the structure of the modulators. Such compounds, which may include peptidomimetics of peptide modulators, may be used in the same manner as the initial modulators. An inhibitor, or activator may be one which exerts its lin-14 or lin-4 function or expression. In one embodiment, the inhibition or activation by an identified modulator results in the modulation of lin-14 or lin-4 biological activity or expression as compared to that observed in the absence of the added test compound.

II. Methods and Materials for Manufacture and Formulation

A. Nucleic Acids General Techniques and Materials

General texts which describe molecular biological techniques include Sambrook, Molecular Cloning: a Laboratory Manual (2$^{nd}$ ed.) Vols. 1-3, Cold Spring Harbor Laboratory, (1989); Current Protocols in Molecular Biology Ausubel, ed. John Wiley & Sons, Inc., New York (1997); Laboratory Techniques in Biochemistry and Molecular Biology: Hybridization With Nucleic Acid Probes, *Part 1. Theory and Nucleic Acid Preparation*, P. Tijssen, ed. Elsevier, N.Y. (1993); Berger and Kimmel, Guide to Molecule Cloning Techniques Methods in Enzymology volume 152 Academic Press, Inc., San Diego, Calif. These texts describe the synthesis of nucleic acids as well as mutagenesis, the use of vectors, promoters and many other relevant topics related to, e.g., the generation and expression of genes that encode lin-14 or lin-4 or other miRNA activity. Techniques for isolation, purification and manipulation of nucleic acids, genes, such as generating libraries, subcloning into expression vectors, labeling probes, and DNA hybridization are also described in the texts above and are well known to one of ordinary skill in the art.

The nucleic acids, whether miRNA, DNA, cDNA, or genomic DNA, or a variant thereof, may be isolated from a variety of sources or may be synthesized in vitro. Nucleic acids as described herein can be administered to or expressed in human, transgenic animals, transformed cells, in a transformed cell lysate, or in a partially purified or a substantially pure form.

Nucleic acids are detected and quantified in accordance with any of a number of general means well known to those of skill in the art. These include, for example, analytical biochemical methods such as spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immuno-fluorescent assays, and the like, Southern analysis, Northern analysis, Dot-blot analysis, gel electrophoresis, RT-PCR, quantitative PCR, other nucleic acid or target or signal amplification methods, radiolabeling, scintillation counting, and affinity chromatography.

Various types of mutagenesis can be used, e,g., to modify a nucleic acid encoding a gene with lin-4, let-7 or other miRNA activity. They include, but are not limited to, site-directed, random point mutagenesis, homologous recombination (DNA shuffling), mutagenesis using uracil containing templates, oligonucleotide-directed mutagenesis, phosphorothioate-modified DNA mutagenesis, and mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, are also included. In one embodiment, mutagenesis can be guided by known information of the naturally occurring molecule or altered or mutated naturally occurring molecule, e.g., sequence, sequence comparisons, physical properties, crystal structure or the like. Changes may be made to increase the activity of the miRNA, to increase its biological stability or half-life, and the like.

Comparative hybridization can be used to identify nucleic acids encoding genes with lin-4, let-7 or other miRNA activity, including conservative variations of nucleic acids. Nucleic acids "hybridize" when they associate, typically in solution. Nucleic acids hybridize due to a variety of well characterized physico-chemical force, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes part I chapter 2, "Overview of principles of hybridization and the strategy of nucleic acid probe assays," (Elsevier, N.Y.), as well as in Ausubel, supra. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Suitable nucleic acids for use in the methods described herein include, but are not limited to, pri-miRNA, pre-miRNA, mature miRNA or fragments of variants thereof that retain the biological activity of the miRNA and DNA encoding a pri-miRNA, pre-miRNA, mature miRNA, fragments or variants thereof, or DNA encoding regulatory elements of the miRNA.

In one embodiment the nucleic acid encoding the disclosed inhibitory nucleic acids, for example an miRNA molecule, is on a vector. These vectors include a sequence encoding a mature microRNA and in vivo expression elements. In a preferred embodiment, these vectors include a sequence encoding a pre-miRNA and in vivo expression elements such that the pre-miRNA is expressed and processed in vivo into a mature miRNA. In another embodiment, these vectors include a sequence encoding the pri-miRNA gene and in vivo expression elements. In this embodiment, the primary transcript is first processed to produce the stem-loop precursor miRNA molecule. The stem-loop precursor is then processed to produce the mature microRNA. Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have generally utility for the high-efficiency transduction of nucleic acids in vivo. Standard protocols for producing replication-deficient retroviruses (including the steps of incorporation of exogenous genetic material into a plasmid, transfection of a packaging cell lines with plasmid, production of recombinant retroviruses by the packaging cell lie, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N.J. (1991).

The "in vivo expression elements" are any regulatory nucleotide sequence, such as a promoter sequence or promoter-enhancer combination, which facilitates the efficient expression of the nucleic acid to produce the microRNA. The in vivo expression element may, for example, be a mammalian or viral promoter, such as a constitutive or inducible promoter or a tissue specific promoter, examples of which are well known to one of ordinary skill in the art. Constitutive mammalian promoters include polymerase promoters as well as the promoters for the following genes: hypoxanthine phosphoribosyl transferase (HPTR), adenosine deaminase, pyruvate kinase, and beta-actin. Exemplary viral promoters which function constitutively in eukaryotic cells include promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include metal-inducible promoters and steroid-regulated promoters. For example, the metallothionein promoters is induced to promote transcription in the presence of certain metal ion. Other inducible promoters are known to those of ordinary skill in the art.

Examples of tissue-specific promoters include the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol 7-alpha hydroylase (CYP-7) promoter, beta-galactosidase alpha-2,6 sialyltransferase promoter, insulin-like growth factor binding protein (IGFBP-1) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human H+/K+-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include the uteroglobin promoter. Exemplary tissue-specific expression elements for adrenal cells include cholesterol side-chain cleavage (SCC) promoter. Exemplary tissue-specific expression elements for the general nervous system include gamma-gamma enolase (neuron-specific enolase, NSE) promoter. Exemplary tissue-specific expression elements for the brain include the neurofilament heavy chain (NF-H) promoter. Exemplary tissue-specific expression elements for lymphocytes include the human CGL-1/granzyme B promoter, the terminal deoxy transferase (TdT), lambda 5, VpreB, and lck (lymphocyte specific tyrosine protein kinase p561ck) promoter, the humans CD2 promoter and its 3' transcriptional enhancer, and the human NK and T cell specific activation (NKG5) promoter. Exemplary tissue-specific expression elements for the colon include pp60c-src tyrosine kinase promoter, organ-specific neoantigens (OSNs) promoter, and colon specific antigen-P promoter. Exemplary tissue-specific expression elements for breast cells include the human alpha-lactalbumin promoter. Exemplary tissue-specific expression elements for the lung include the cystic fibrosis transmembrane conductance regulator (CFTR) gene promoter. Other elements aiding specificity of expression in a tissue of interest can include secretion leader sequences, enhancers, nuclear localization signals, endosmolytic peptides, etc. Preferably, these elements are derived from the tissue of interest to aid specificity.

In general, the in vivo expression element shall include, as necessary, 5' non-transcribing and 5' non-translating sequences involved with the initiation of transcription. They optionally include enhancer sequences or upstream activator sequences.

The miRNA can be isolated from cells or tissues, recombinantly produced, or synthesized in vitro by a variety of techniques well known to one of ordinary skill in the art. In one embodiment, miRNA is isolated from cells or tissues. Techniques for isolating miRNA from cells or tissues are well known to one of ordinary skill in the art. For example, miRNA can be isolated from total RNA using the mirVana miRNA isolation kit from Ambion, Inc. Another techniques utilizes the flashPAGE™ Fractionator System (Ambion, Inc.) for PAGE purification of small nucleic acids.

The miRNA can be obtained by preparing a recombinant version thereof (i.e., by using the techniques of genetic engineering to produce a recombinant nucleic acid which can then be isolated or purified by techniques well known to one of ordinary skill in the art). This embodiment involves growing a culture of host cells in a suitable culture medium, and purifying the miRNA from the cells or the culture in which the cells are grown. For example, the methods include a process for producing a miRNA in which a host cell containing a suitable expression vector that includes a nucleic acid encoding an miRNA is cultured under conditions that allow expression of the encoded miRNA. In a preferred embodiment the nucleic acid encodes lin-4 or let-7. The miRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the miRNA into the host cell can be effected by calcium phosphate transfection, DEAE, dextran mediated transfection, or electroporation (Davis, L. et al., Basic Methods in Molecular Biology (1986)).

Any host/vector system can be used to express one or more of the miRNAs. These include eukaryotic hosts such as HeLa cells and yeast, as well as prokaryotic host such as E. coli and B. subtilis. miRNA can be expressed in mammalian cells, yeast, bacteria, or other cells where the miRNA gene is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In the preferred embodiment, the miRNA is expressed in mammalian cells. Examples of mammalian expression systems include C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors will comprise an origin of replication, a suitable promoter polyadenylation site, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Potentially suitable yeast strains include *Saccharomyces cerevisiae, Schizosaccharomyces pombe, Kluyveromyces* strains, *Candida*, or any yeast strain capable of expressing miRNA. Potentially suitable bacterial strains include *Escherichia coli, Bacillus subtilis, Salmonella typhimurium*, or any bacterial strain capable of expressing miRNA.

In a preferred embodiment, genomic DNA encoding lin-4 is isolated, the genomic DNA is expressed in a mammalian expression system, and RNA is purified and modified as necessary for administration to a individual. In a preferred embodiment the lin-4 is in the form of a pre-miRNA, which can be modified as desired (i.e. for increased stability or cellular uptake).

Knowledge of DNA sequences of miRNA allows for modification of cells to permit or increase expression of an endogenous miRNA. Cells can be modified (e.g. by homologous recombination) to provide increased miRNA expression by replacing, in whole or in part, the naturally occurring promoter with all or part of a heterologous promoter so that the cells express the miRNA at higher levels. The heterologous promoter is inserted in such a manner that it is operatively linked to the desired miRNA encoding sequences. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also may be engineered to express an endogenous gene comprising the miRNA under the control of inducible regulatory elements, in which case the regulatory sequences of the endogenous gene may be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al.

The miRNA may be prepared by culturing transformed host cells under culture conditions suitable to express the miRNA. The resulting expressed miRNA may then be purified from such culture (i.e., from culture medium or cell extracts) using known purification processes such as gel filtration and ion exchange chromatography. The purification of the miRNA may also include an affinity column containing agents which will bind to the protein; one or more column steps over such affinity resins as concanavalin A-agarose, heparin-toyopearl™ or Cibacrom blue 3GA Sepharose™; one or more steps involving hydrophobic interaction chromatography using such resins as phenyl ether, butyl ether, or propyl ether; immunoaffinity chromatography, or complementary cDNA affinity chromatography.

The miRNA may also be expressed as a product of transgenic animals, which are characterized by somatic or germ cells containing a nucleotide sequence encoding the miRNA. A vector containing DNA encoding miRNA and appropriate regulatory elements can be inserted in the germ line of animals using homologous recombination (Capecchi, Science 244:1288-1292 (1989)), such that the express the miRNA. Transgenic animals, preferably non-human mammals, are produced using methods as described in U.S. Pat. No. 5,489,743 to Robinson, et al., and PCT Publication No. WO 94/28122 by Ontario Cancer Institute. miRNA can be isolated from cells or tissue isolated from transgenic animals as discussed above.

In a preferred embodiment, the miRNA can be obtained synthetically, for example, by chemically synthesizing a nucleic acid by any method of synthesis known to those skilled artisan. The synthesized miRNA can then be purified by any method known in the art. Methods for chemical synthesis of nucleic acids include in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages may be preferred. Nucleic acids containing modified internucleoside linkages may also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2$), diinethylene-sulfoxide ($-CH_2-SO-CH_2$), dimethylene-sulfone ($-CH_2-SO_2-CH_2$), 2'-O-alkyl, and 2'-deoxy-2'-fluoro phosphorothioate internucleoside linkages are well known in the art (see Uhlmann et al., 1990, *Chem. Rev.* 90:543-584; Schneider et al., 1990, *Tetra-*

*hedron Lett.* 31:335 and references cited therein). U.S. Pat. Nos. 5,614,617 and 5,223,618 to Cook, et al., U.S. Pat. No. 5,714,606 to Acevedo, et al., U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmaeker, et al., U.S. Pat. No. 5,610,289 to Cook, et al., and U.S. Pat. No. 5,858,988 to Wang, also describe nucleic acid analogs for enhanced nuclease stability and cellular uptake.

III. Screening

A. Methods for Screening for Modulators

Methods for identifying modulators of the function, expression, or bioavailability of lin-14 or lin-4 or other genes described herein and homologues thereof, in particular the function of lin-14 mRNA or LIN-14 or lin-4 miRNA, utilize well known techniques and reagents. The modulator can modulate lin-14 or lin-4 function in the insulin-like signaling pathway, for example to alter lifespan, senescence, cell survivability, or inhibit age-related disorders. Modulation of lin-14 or lin-4 can be direct or indirect. Direct modulation refers to a physical interaction between the modulator and lin-14 or lin-4 mRNA, protein, miRNA or DNA. Indirect modulation of lin-14 or lin-4 can be accomplished when the modulator physically associates with a cofactor, second protein or second biological molecule that interacts with lin-14 or lin-4 mRNA, miRNA, DNA or protein either directly or indirectly. Additionally, indirect modulation includes modulators that affect the expression of the translation of RNA encoding lin-14 or lin-4.

In some embodiments, the assays can include random screening of large libraries of test compounds. Alternatively, the assays may be used to focus on particular classes of compounds suspected of modulating the function or expression of lin-14 or lin-4 or homologues thereof in cells, tissues, organs, or systems.

Assays can include determinations of lin-14 or lin-4 expression, protein expression, protein activity, or binding activity. Other assays can include determinations of lin-14 or lin-4 nucleic acid transcription or translation, for example mRNA levels, miRNA levels, mRNA stability, mRNA degradation, transcription rates, and translation rates.

In one embodiment, the identification of a lin-14 or lin-4 modulator is based on the function of LIN-14 or lin-4 miRNA in the presence and absence of a test compound. The test compound or modulator can be any substance that alters or is believed to alter the function of lin-14 or lin-4, in particular the function of lin-14 or lin-4 in the insulin-like signaling pathway. Typically, a modulator will be selected that reduces, eliminates, or inhibits, lin-14 mediated insulin signaling or increases or enhances lin-4 expression or function.

One exemplary method includes contacting LIN-14 or lin-4 miRNA with at least a first test compound, and assaying for an interaction between LIN-14 or lin-4 miRNA and the first test compound with an assay. The assaying can include determining insulin-like signaling, cell survivability, or lifespan assays.

Specific assay endpoints or interactions that may be measured in the disclosed embodiments include assaying for insulin-like signaling or lifespan modulation, lin-14 or lin-4 down or up regulation or turnover. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms such as *C. elegans* and transgenic animals.

Other screening methods include using labeled LIN-14 or lin-4 miRNA to identify a test compound. LIN-14 lin-4 miRNA can be labeled using standard labeling procedures that are well known and used in the art. Such labels include, but are not limited to, radioactive, fluorescent, biological and enzymatic tags.

Another embodiment provides a method for identifying a modulator of lin-14 or lin-4 expression by determining the effect a test compound has on the expression of lin-14 or lin-4 in cells. For example isolated cells or whole organisms expressing lin-14, lin-4 or both can be contacted with a test compound. Lin-14 or lin-4 expression can be determined by detecting LIN-14 protein expression of lin-14 or lin-4 mRNA transcription or translation. Suitable cells for this assay include, but are not limited to, immortalized cell lines, primary cell culture, or cells engineered to express lin-14 or lin-4, for example cells from *C. elegans*. Compounds that modulate the expression of lin-14, in particular that reduce or inhibit the expression or bioavailability of lin-14, can be selected. Alternatively, compounds that increase or enhance lin-4 expression or activity can be selected.

Still another embodiment provides a method for screening or identifying anti-aging compounds and anti-aging gene targets using *C. elegans* heterochronic mutants such as lin-4, lin-14, lin-28, egl-35, let-7, lin-42 as well as mutants of any homologues, for example mir-125, in any species. Representative additional species include, but are not limited to *Drosophila*, mouse, and zebrafish. Heterochronic mutants can be screened as discussed above. For example, cells from a heterochronic mutant, or heterochronic mutant organisms can be contacted with a test compound. The survivability of the cell or heterochronic mutant organism contacted with the compound can be compared to control cells or organisms not contacted with the test compound. Compounds that increase the survivability of the heterochronic mutant cells or organisms relative to controls can be selected.

Another embodiment provides for in vitro assays for the identification of lin-14 or lin-4 modulators or modulators of lin-14 or lin-4 homologues. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule, for example a nucleic acid encoding LIN-14 or lin-4 miRNA, in a specific fashion is strong evidence of a related biological effect. Such a molecule can bind to a lin-14 or lin-4 nucleic acid and modulate expression of lin-14 or lin-4, for example up-regulate expression of lin-4 or downregulate lin-14. The binding of a molecule to a target may, in and of itself, be inhibitory, due to steric, allosteric or charge-charge interactions or may downregulate or inactivate LIN-14 or lin-4 miRNA. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

Other embodiments include methods of screening compounds for their ability to modulate lin-14, lin-4 or homologues thereof in cells. Various cell lines can be utilized for such screening assays, including cells specifically engineered for this purpose. Suitable cells include C. elegans. Cells can also be engineered to express lin-14, lin-4 or a modulator thereof or a combination of both lin-14/lin-4 or a modulator of lin-14/lin-4. Furthermore, those of skill in the art will appreciate that stable or transient transfections, which are well known and used in the art, may be used in the disclosed embodiments.

For example, a transgenic cell comprising an expression vector can be generated by introducing the expression vector into the cell. The introduction of DNA into a cell or a host cell is well known technology in the field of molecular biology and is described, for example, in Sambrook et al., Molecular Cloning 3rd Ed. (2001). Methods of transfection of cells include calcium phosphate precipitation, liposome mediated transfection, DEAE dextran mediated transfection, electroporation, ballistic bombardment, and the like. Alternatively, cells may be simply transfected with the disclosed expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE, La Jolla, Calif.). Alternatively bacterial cells such as E. coli LE392 could be used as host cells for phage viruses. Eukaryotic cells that can be used as host cells include but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector. Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

In vivo assays involve the use of various animal models, including non-human transgenic animals that have been engineered to have specific defects, or carry markers that can be used to measure the ability of a test compound to reach and affect different cells within the organism. Due to their size, ease of handling, and information on their physiology and genetic make-up, mice are a preferred embodiment, especially for transgenic animals. However, other animals are suitable as well, including C. elegans, rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more test compounds are administered to an animal, and the ability of the test compound(s) to alter one or more characteristics, as compared to a similar animal not treated with the test compound(s), identifies a modulator. Other embodiments provide methods of screening for a test compound that modulates the function of lin-14 or lin-4. In these embodiments, a representative method generally includes the steps of administering a test compound to the animal and determining the ability of the test compound to reduce one or more characteristics of aging, lifespan, or age-related disorder.

Treatment of these animals with test compounds will involve the administration of the compound, in an appropriate form, to the animal. Administration will be by any route that could be utilized for clinical or non-clinical purposes, including, but not limited to, oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

B. Screening for Genes or Mutations Involved in Aging

One embodiment provides a method for increasing survivability of cell by contacting the cell with an inhibitory nucleic acid that binds and inhibits expression of aging genes like lin-14 in an amount effective to alter insulin-like signaling. The survivability of the cell can be compared to survivability of a cell that is not contacted with the inhibitory nucleic acid. Representative inhibitory nucleic acids include, but are not limited to lin-4 miRNA, mi-125a, mi-125b variants and homologues thereof. This method can be used to identify compounds that are effective to modulate the activity of the identified genes, allowing isolation of compounds that can enhance or inhibit activity of the genes.

Screening can also be used to identify other genes or mutations in genes that are involved in aging, where the cells having modifications to the other genes are identified by differences in gene sequence, expression or activity as compared to normal or control genes. For example, cells from an individual with an Age related disorder such as Parkinson's can be screened for lin-4 miRNA, mi-125a, mi-125b variants or variants of the human homologues thereof, by comparison with known sequences or sequences from normal cells. Normal cells may be cells from an individual not having an age related disorder or they may be cells from someone who has been identified by, for example, an exceptionally long life span, or disease free old age, or who is young (which may be defined as in a stage of development wherein cells are still proliferating or growth is still occurring).

C. Diagnostics

With the knowledge of the role of Lin-14 and homologues thereof in aging and age-related disorders, it is possible to screen for individuals who are at risk of, or in the early stages of development of, age-related disorders, to identify those individuals who should be treated with other therapeutics to minimize or delay onset of the age-related disorders.

Levels of lin-42, egl-35, lin-28, let-7, lin-14 or lin-4 nucleic acid or protein can be determined and quantified using conventional techniques including for example, PCR and ELISA assays. The level of lin-14 or lin-4 nucleic acid or protein in a test sample can be compared to the level of lin-14 or lin-4 nucleic acid or protein in a control sample. Variations in the levels of lin-14 or lin-4 nucleic acid or protein in the test sample compared to the control sample can be correlated with a pathology. For example, increased levels of lin-14 nucleic acid or other genes described herein and homologues thereof or protein in the test sample relative to the control sample can be indicative of an age-related disorder or a propensity to develop an age-related disorder. Alternatively, decreased levels of lin-4 nucleic acid or protein in the test sample relative to the control sample can be indicative of an age-related disorder or a propensity to develop an age-related disorder.

Alternatively, levels of lin-4 can be detected and quantified in a test sample using conventional techniques. The level of lin-4 in the test sample can be compared to normal age controls. Low levels of lin-4 can be correlated with age-related disorders or the propensity to develop age-related disorders.

IV. Methods of Treatment or Prevention

A. Disorders to be Treated

Age-related disorders include Alzheimer's disease, Parkinson's disease, arthritis, stroke, dementia, memory loss, diabetes, and heart disease. Premature aging may also be an age-related disorder, where a person appears to be older than average for a particular age. The compositions described herein can be administered in effective dosages, alone or in combination with a second therapeutic, for an age-related disorder to improve at least one symptom or manifestation of the disease. As used herein, "improve" means to inhibit the rate of development, stop development, or reverse development of a symptom or characteristic of the disorder. The compositions can be used to treat, alleviate, reduce, or inhibit age-related disorders, senescence, or symptoms thereof. The symptoms of aging affect the human body in both physical and mental ways. Aging of cells and tissues can affect a person's strength, stamina and agility. Aging of various cells and tissues can result in the diminished sensations of well-being, fatigue, delayed physical and mental recovery, diminished cognitive ability and insomnia. Further physical effects include skin aging, wrinkling, and discoloration, hair loss, decreased endurance and tolerance to physical and mental activities, and muscle fatigue. Neuro-endocrinological disorders, such as decreased sexual performance and maintenance of normal blood pressure and blood chemistry, are also closely associated with the aging of tissues. The disclosed compositions can be used to treat or inhibit one or more of these age-related disorders or symptoms thereof.

In addition, compounds, including therapeutic nucleic acids such as lin-4 or homologues thereof or modulators of lin-14, may be used for prophylactic treatment of age-related disorders. Under these circumstances, it may be beneficial to treat these individuals with therapeutically effective doses of the nucleic acids or modulators to reduce the risk of developing age-related disorders. In other embodiments, the nucleic acid or modulator in a suitable formulation is administered to a subject who has reached a particular age, for example age 40 or more. In yet other embodiments, the nucleic acid or modulator in a suitable formulation is administered to subjects who exhibit symptoms of age-related disorders (e.g., early or advanced). In still other embodiments, the nucleic acid in a suitable formulation may be administered to a subject as a preventive measure. In some embodiments, the nucleic acid in a suitable formulation may be administered to a subject based on demographics or epidemiological studies, or to a subject in a particular field or career.

The compounds can be administered to a host in an amount effective to treat or inhibit senescence or age-related disorder, for example by altering the insulin-like signal pathway. Altering the insulin-like signal pathway can extend the lifespan of certain cells and thereby treat, alleviate, or inhibit age-related disorders. Exemplary cells that can have increased lifespan in response to the disclosed compositions include, but are not limited to neural cells, cardiac cells, smooth muscle cells, muscle cells, epidermal cells, somatic cells, and postmitotic cells.

B. Formulations

The compositions are administered to a individual in need of treatment or prophylaxis of at least one symptom or manifestation (since disease can occur/progress in the absence of symptoms) of an age-related disorder or senescence. In one embodiment, the compositions are administered in an effective amount to inhibit gene expression of aging genes like lin-14 or homologues thereof mentioned in this application. Alternatively, a composition is administered in an amount effective to increase or enhance gene expression of lin-4 or homologues thereof. In preferred embodiments, the compositions are administered in an effective amount to alter the insulin-like signaling pathway.

The compounds are preferably employed for therapeutic uses in combination with a suitable pharmaceutical carrier. Such compositions comprise an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids some of which are described herein.

It is understood by one of ordinary skill in the art that nucleic acids administered in vivo are taken up and distributed to cells and tissues (Huang, et al., *FEBS Lett.* 558(1-3): 69-73 (2004)). For example, Nyce et al. have shown that antisense oligodeoxynucleotides (ODNs) when inhaled bind to endogenous surfactant (a lipid produced by lung cells) and are taken up by lung cells without a need for additional carrier lipids (Nyce and Metzger, *Nature*, 385:721-725 (1997). Small nucleic acids are readily taken up into T24 bladder carcinoma tissue culture cells (Ma, et al., *Antisense Nucleic Acid Drug Dev.* 8:415-426 (1998). siRNAs have been used for therapeutic silencing of an endogenous genes by systemic administration (Soutschek, et al., *Nature* 432, 173-178 (2004)).

The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or microspheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example in Sambrook et al., 1989, *Molecular Cloning: A Laboratory Manual*, Cold Spring Harbor Laboratory, New York; and Ausubel et al., 1994, *Current Protocols in Molecular Biology*, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. By way of example, and not by limitation, the nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, with vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative. The compositions may taken such forms as.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oil. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose any bland fixed oil may be employed including synthetic mono- or di-glycerides. In addition, fatty acids such as oleic acid may be used in preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compound alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. For administration by inhalation, the compound are conveniently delivered in the form of an aerosol spray presentation from pressurized packs or a nebulizer, with the use of a suitable propellant.

In some embodiments, the compound described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, stabilizers. In one embodiment, the compounds are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Bioorg. Med. Chem. Lett.* 14(19):4975-4977 (2004)) and in vivo (Soutschek, et al., *Nature* 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.* 59(11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe(II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et. al., also described methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

The formulations described herein of the nucleic acids embrace fusions of the nucleic acids or modifications acids, wherein the nucleic acid is fused to another moiety or moieties, e.g., targeting moiety or another therapeutic agent. Such analogs may exhibit improved properties such as activity and/or stability. Examples of moieties which may be linked or unlinked to the nucleic acid include, for example, targeting moieties which provide for the delivery of nucleic acid to specific cells, e.g., antibodies to pancreatic cells, immune cells, lung cells or any other preferred cell type, as well as receptor and ligands expressed on the preferred cell type. Preferably, the moieties target cancer or tumor cells. For example, since cancer cells have increased consumption of glucose, the nucleic acids can be linked to glucose molecules. Monoclonal humanized antibodies that target cancer or tumor cells are preferred moieties and can be linked or unlinked to the nucleic acids. In the case of cancer therapeutics, the target antigen is typically a protein that is unique and/or essential to the tumor cells (e.g., the receptor protein HER-2).

C. Methods of Administration

In general, methods of administering compounds, including nucleic acids, are well known in the art. In particular, the routes of administration already in use for nucleic acid therapeutics, along with formulations in current use, provide preferred routes of administration and formulation for the nucleic acids described above.

Compositions can be administered by a number of routes including, but not limited to: oral, intravenous, intraperitoneal, intramuscular, transdermal, subcutaneous, topical, sublingual, or rectal means. Compounds can also be administered via liposomes. Such administration routes and appropriate formulations are generally known to those of skill in the art.

Administration of the formulations described herein may be accomplished by any acceptable method which allows the compounds, for example miRNA or nucleic acid encoding the miRNA, to reach its target. The particular mode selected will depend of course upon factors such as the particular formulation, the severity of the state of the subject being treated, and the dosage required for therapeutic efficacy. As generally used herein, an "effective amount" is that amount which is able to treat one or more symptoms of age related disorder, reverse the progression of one or more symptoms of age related disorder, halt the progression of one or more symptoms of age related disorder, or prevent the occurrence of one or more symptoms of age related disorder in a subject to whom the formulation is administered, as compared to a matched subject not receiving the compound. The actual effective amounts of compound can vary according to the specific compound or combination thereof being utilized, the particular composition formulated, the mode of administration, and the age, weight, condition of the individual, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. The composition can be injected intradermally for treatment or prevention of age related disorder, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The nucleic acid may be delivered in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the miRNA over a certain time period, for example, hours, days, weeks, months or years. This may be accomplished, for example, by repeated administrations of a formulation or by a sustained or controlled release delivery system in which the miRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other deliver systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the miRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing miRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapusule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

D. Effective Dosages

Dosages for a particular individual can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a individual is sufficient to effect a beneficial therapeutic response in the individual over time, or, e.g., to reduce symptoms, or other appropriate activity, depending on the application. The dose is determined by the efficacy of the particular formulation, and the activity, stability or serum half-life of the miRNA employed and the condition of the individual, as well as the body weight or surface area of the individual to be treated. The size of the dose is also determined by the existence, nature, and extent of any adverse side-effects that accompany the administration of a particular vector, formulation, or the like in a particular individual.

Therapeutic compositions comprising one or more nucleic acids are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the individual. Administration can be accomplished via single or divided doses.

In vitro models can be used to determine the effective doses of the nucleic acids as a potential age related disorder treatment, as described in the examples. In determining the effective amount of the compound to be administered in the treatment or prophylaxis of disease the physician evaluates circulating plasma levels, formulation toxicities, and progression of the disease. For nucleic acids, the dose administered to a 70 kilogram individual is typically in the range equivalent to dosages of currently-used therapeutic antisense oligonucleotides such as Vitravene® (fomivirsen sodium injection) which is approved by the FDA for treatment of cytomegaloviral RNA, adjusted for the altered activity or serum half-life of the relevant composition.

The formulations described herein can supplement treatment conditions by any known conventional therapy, including , but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the nucleic acids can also be administered in therapeutically effective amounts as a portion of an anti-age-related disorder cocktail. Anti-aging cocktails can include, therapeutics to treat Alzheimer's disease, Parkinson's disease, stroke, high blood pressure, dementia, heart disease, and arthritis.

EXAMPLES

The present invention will be further understood by reference to the following non-limiting examples.

Experimental Procedures

Strains. The *C. elegans* strains used were as follows: wild-type N2 Bristol, lin-4(e912)lf, lin-4(e912)lf, lin-14(n179)lf, lin-14(n355)gf, N2; daf-2(RNAi), lin-14(n179ts); daf-2 (RNAi), N2; daf-16(RNAi), lin-14(n179ts); daf-16(RNAi), N2; lin-14(RNAi), daf-2(e1370), daf-2(e1370); lin-14 (RNAi), daf-16(mu86), daf-16(mu86); (lin-14(RNAi), lin-4 (e912); daf-2(RNAi), daf-16(RNAi), lin-4(e912); daf-16 (RNAi). The lin-4 constructs were injected at 33 ng/μl together with myo-2::gfp (pJKL449.1) at 10 ng/μl to generate lin-4 overexpressing strains.

Lifespan Assays. Unless indicated otherwise, lifespan assays were conducted at 20° C. as previously described (Hsu, A. K., et al. (2003) Science 300, 142). Briefly, synchronized L1s were fed with OP50 or RNAi-expressing HT115 (DE3) bacteria, grown to young adults, and transferred to fresh RNAi plates containing 5-fluorodeoxyuridine (FUDR, 0.1 g/ml) to prevent reproduction. Fresh IPTG-induced RNAi-expressing bacteria were plated onto RNAi plates every 5-7 days. Lifespan was assessed every 2-3 days. Lifespan refers to the time from when animals were plated onto the FDUR plates until they were scored as dead. Animals that no longer responded to repeated, gentle prodding with a platinum wire were scored as dead. Animals that crawled off the plate or burst were excluded from calculations. At least 40 animals were tested for each condition, and at least two independent assays were performed for each lifespan assay. Control and experimental animals were cultured and transferred in parallel.

Autofluorescence Photography. Endogenous gut autofluorescence was photographed using the Endow GFP Longpass filter (exciter: HQ470/4, emitter: HQ500Ip, beamsplitter: Q495Ip). All images were collected on the same day to avoid effects the light source may have on the fluorescence intensity. The images were also collected without using automatic gain control to preserve relative fluorescent intensity levels. All images were handled identically.

Autofluorescence Quantification. Photographs taken as described above were quantified using Axiovision 4.4 software. Briefly, all pixels with brightness greater than background, i.e., only those pixels representing the animal, were chosen for quantification. The average brightness of these pixels was determined for each photograph.

Statistical Analysis. Statistical analysis was carried out using Graphpad Prism 4.0 software to determine survival differences (long-rank test), mean lifespan lengths, and the significance between mean gut autofluorescence values (Mann-Whitney t-test).

EXAMPLE 1 lin-4 and lin-14 Mutants have Opposite Lifespan Phenotypes

Figure 1B:
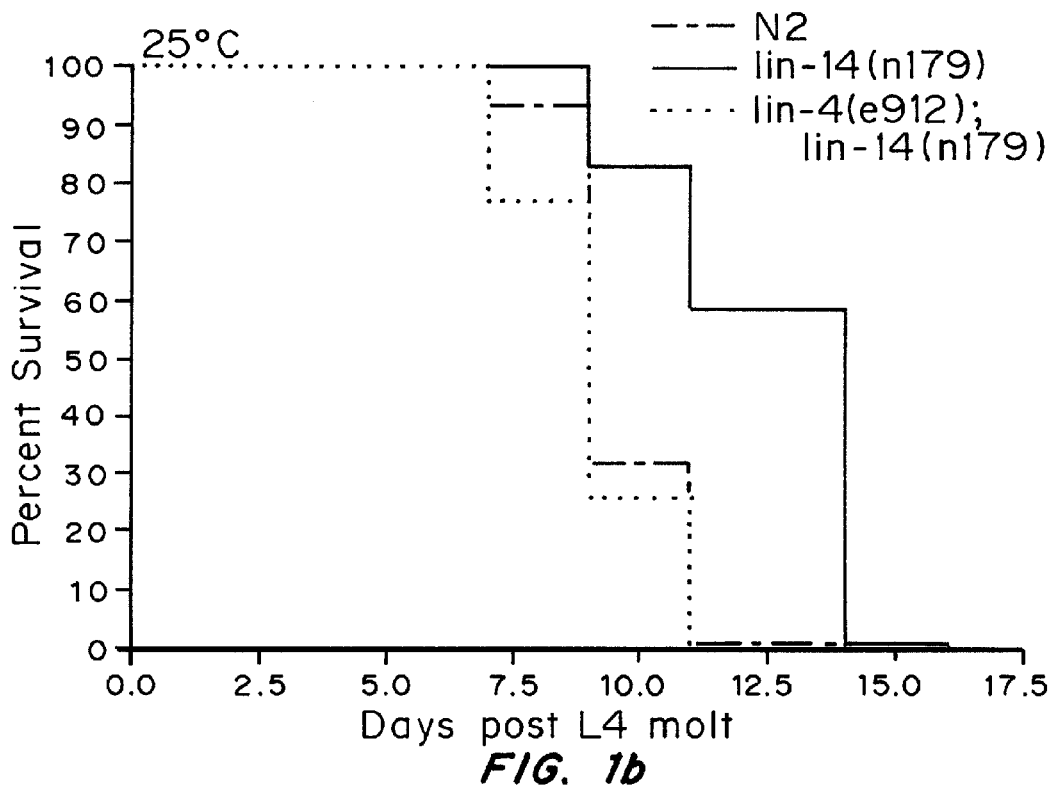
Figure 1C:
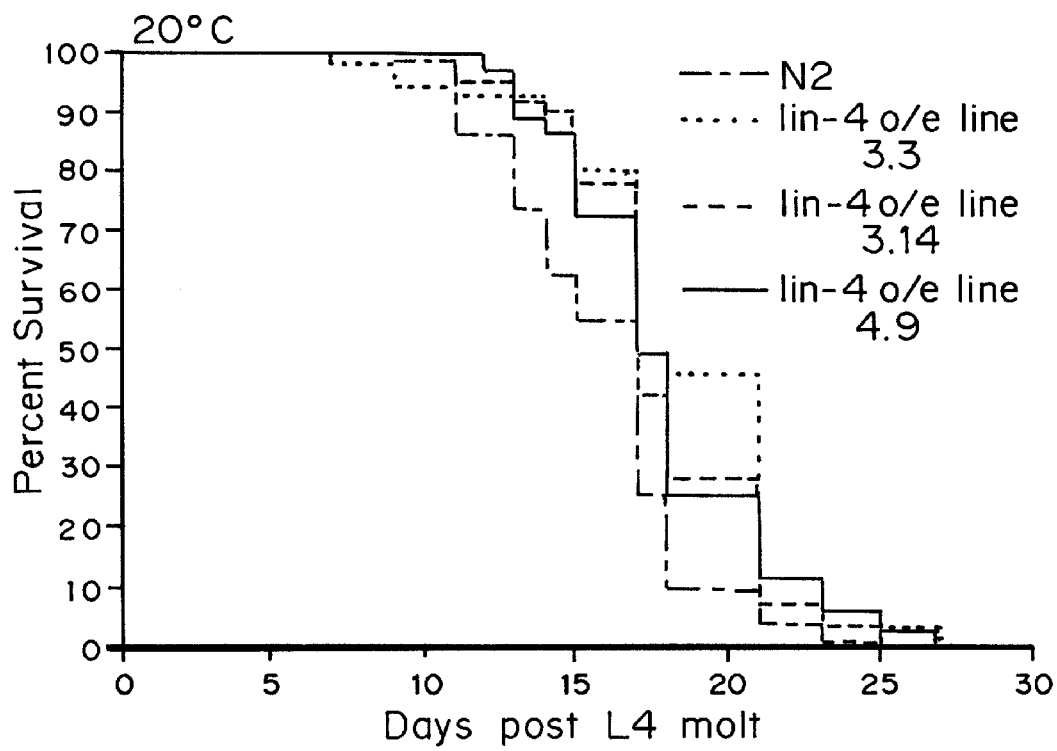
Figure 1D:
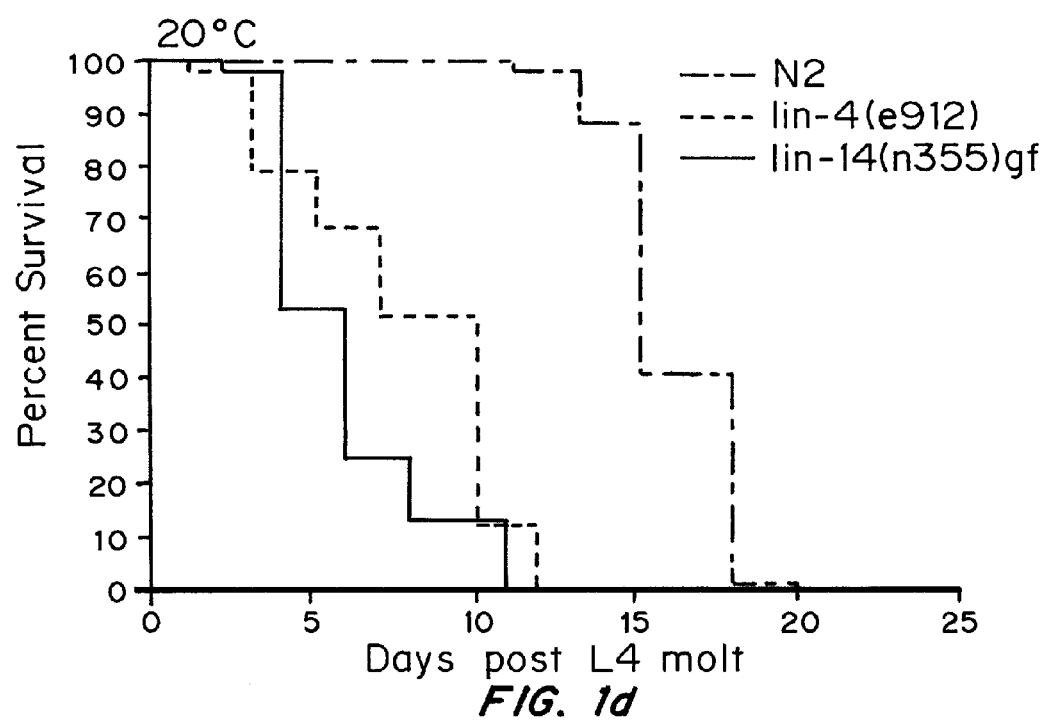

Heterochronic *C. elegans* mutants were assayed for lifespan length. Mutations in lin-4 and lin-14 resulted in aging defects. Animals with a loss-of-function (lf) mutation in lin-4 displayed a lifespan that was significantly shorter than wild-type (FIG. 1A), suggesting that lin-4 is required to prevent premature death. Conversely, overexpressing lin-4 from an extrachromosomal array led to a lengthened lifespan (FIG. 1C). This result demonstrates that the lin-4(lf) mutant did not die prematurely solely due to an unrelated, general pathology, but rather than lin-4 functions to extend lifespan. Consistent with the lin-4 data, a lf mutation in the putative target of lin-4, lin-14, caused the opposite lifespan phenotype. Animals carrying a temperature sensitive lf mutation in lin-14 had a 31% longer lifespan than wildtype (FIG. 1B). The longevity phenotype produced by the lin-14(lf) lesion was reproduced by RNA interference (RNAi) of lin-14 (FIG. 1A). Thus, lin-14 normally acts to promote a short lifespan. A lin-14 gain-of-function (gf) mutant (Wightman, B. et al. (1991) Genes Dev 5, 1813) which lacks the lin-4 complementary sites in the lin-14 3' UTR and overexpresses LIN-14 at later stages (Ruvkun et al., (1983) Nature 338, 313) closely phenocopied the short-lived phenotype of the lin-4(lf) mutant (FIG. 1D). Additionally, lin-14(RNAi) suppressed the short lifespan of the lin-4(e912)lf mutant (FIG. 1A). Taken together, the data suggest that the major role of lin-4 in regulating lifespan is to repress its target, lin-14. All experiments have been repeated at least once with similar effects. n, number of animals observed in each experiment. m, mean adult lifespan (days). P* values refer to experimental strain and N2 control animals in a single experiment, P# values refer to a strain on control and experimental RNAi treatment in a single experiment.

EXAMPLE 2 lin-4(lf) Short Lifespan is Due to Accelerated Aging

Figure 2A:
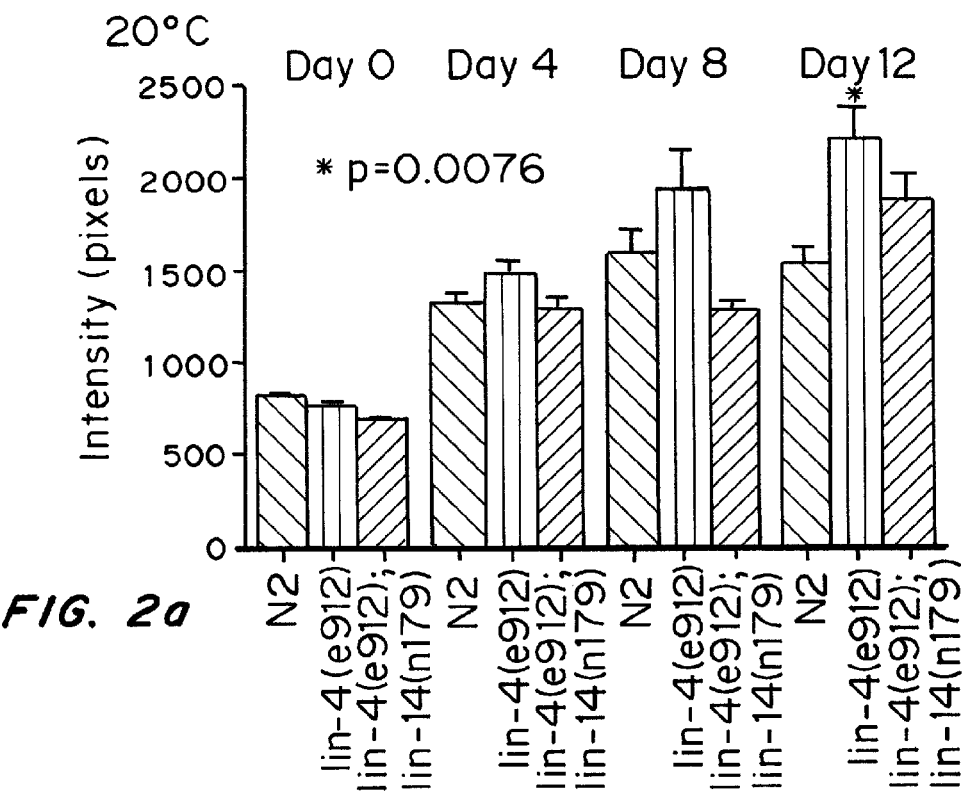
FIGS. 2A and B show bar graphs indicating that accumulation of the aging marker lipofuscin accumulation in lin-4 and lin-14 mutants is accelerated or delayed, respectively.
Figure 2B:
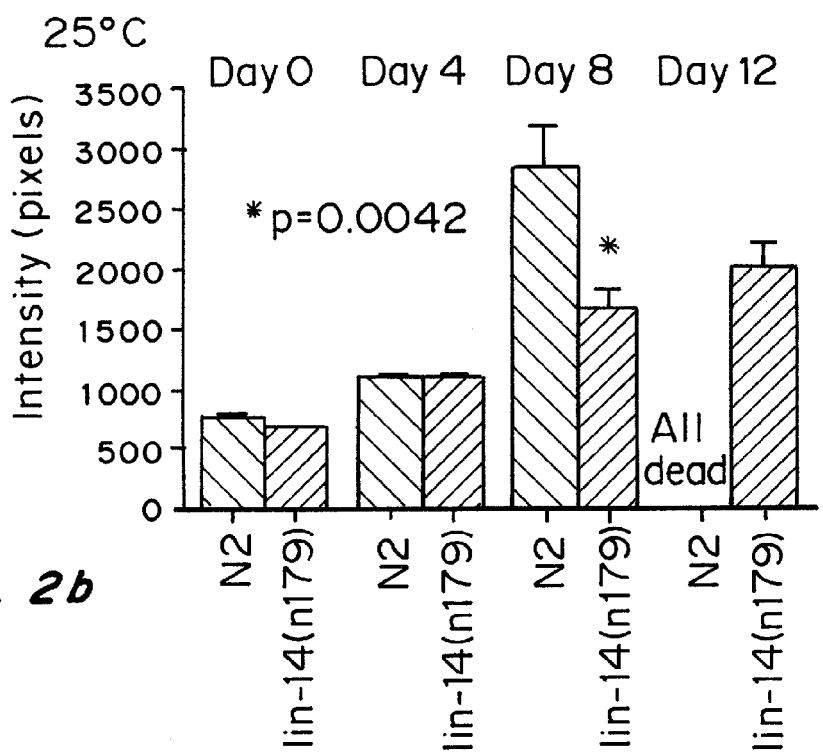
Figure 5A:
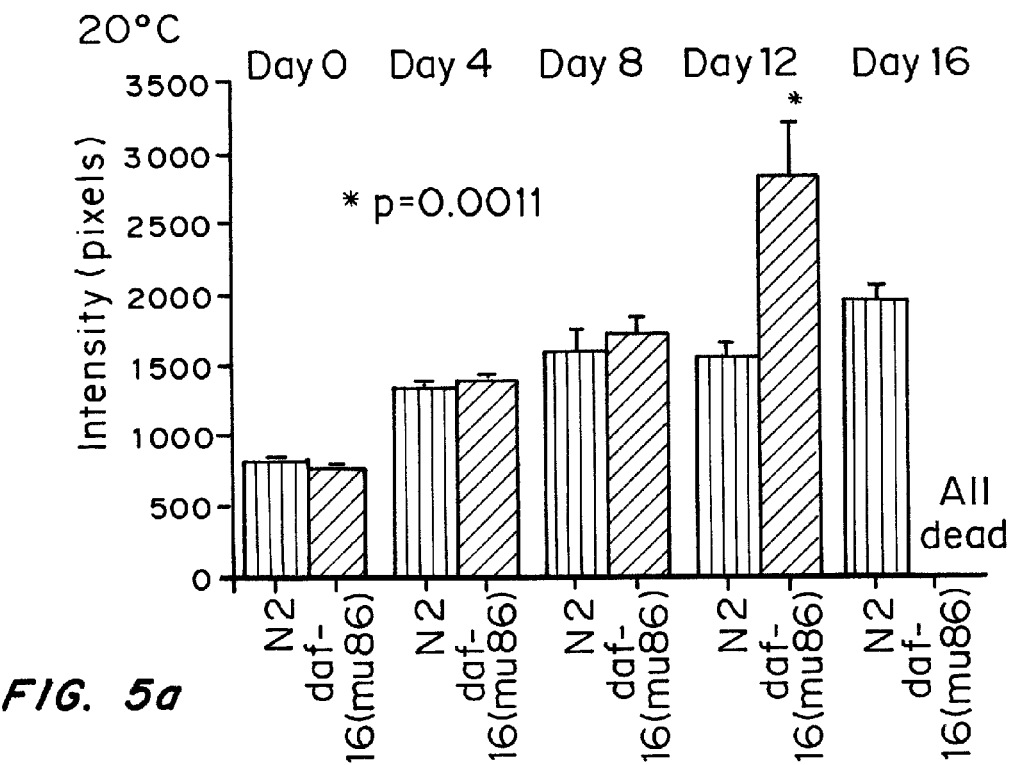
FIGS. 5A and B show bar graphs indicating the accumulation of gut lipofuscin antofluorescence positively correlates with chronological age.
Figure 5B:
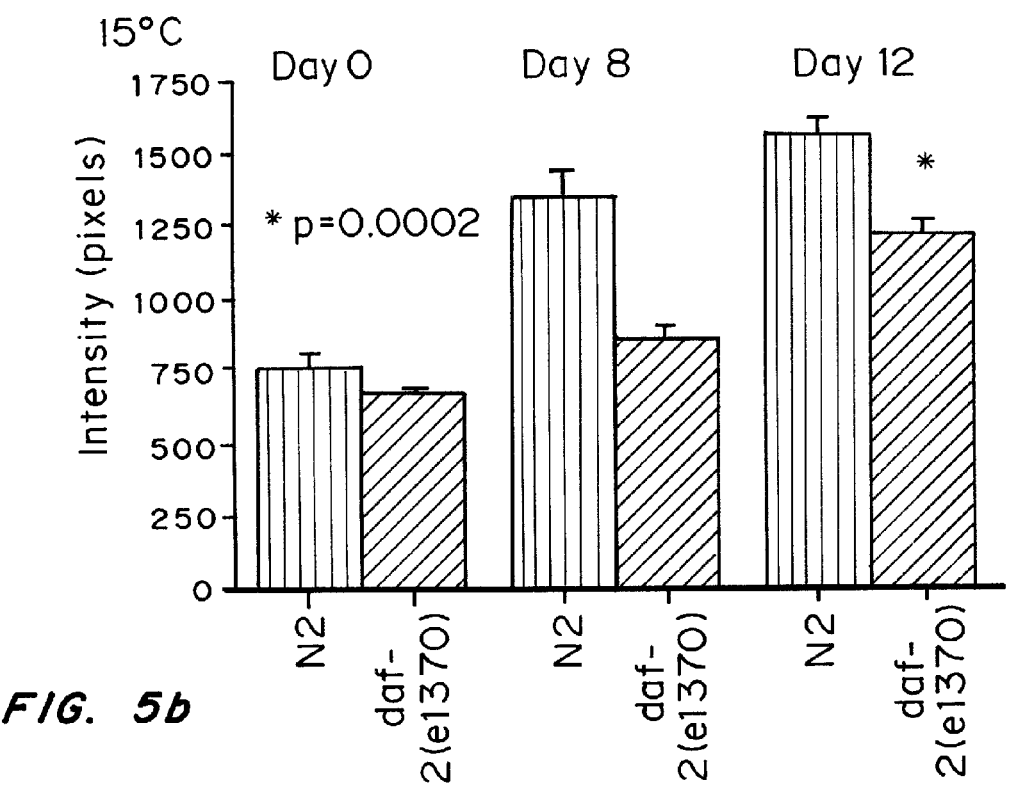

To determine whether the lin-4(lf) short lifespan is due to accelerated aging or to an unrelated, pleiotropic cause, accumulation of intestinal autofluorescence in adult animals was monitored. Intestinal autofluorescence, which is caused by lysosomal deposits of lipofuscin, accumulates over time in the aging worm and is an established marker for aging (Garigan, D. et al., (2002) Genetics 161, 1101). In agreement with its short lifespan, the lin-4(lf) mutant accumulated intestinal autofluorescence more rapidly than wildtype (FIGS. 2A and B). These results resemble those found for the short-lived strain with a daf-16(lf) mutation (FIG. 5B). daf-16 encodes a FOXO transcription factor that regulates lifespan through insulin-like signaling. The premature lipofuscin accumulation caused by lin-4(lf) was suppressed when combined with the lin-14(n179)lf lesion (FIG. 2A), consistent with the ability of lin-14(lf) to suppress the short lifespan of the lin-4(lf) mutant. In contrast to lin-4(lf), the lin-14(n179)lf mutant displayed a slower rate of intestinal autofluorescence accumulation as compared to wildtype (FIG. 2A), in agreement with its extended lifespan. The decreased rate of gut autofluorescence accumulation is similar to that observed in the long-lived daf-2(lf) mutant (FIG. 5B). daf-2 encodes an insulin/IGF-1 receptor that lies upstream of daf-16 in insulin-like signaling.

EXAMPLE 3

The Lifespan Extension of a lin-14(lf) Mutant is hsf-1 Dependent

Figure 6A:
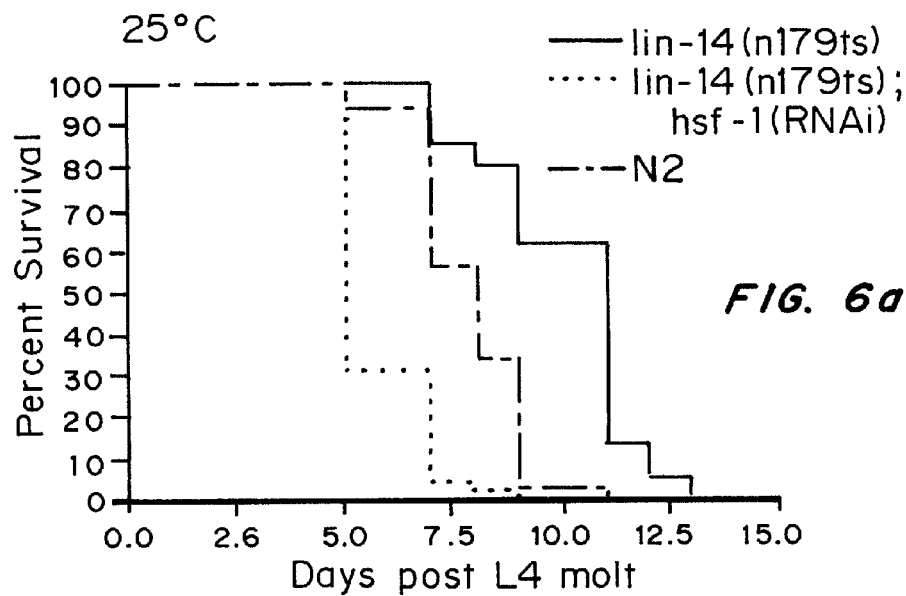
FIG. 6A shows a line graph of days post L4 molt versus percent survival of lin-14(n179ts) and lin-14(n179ts):hsf-1 (RNAi).

C. elegans mutants that display lifespan phenotypes also display altered responses to stress treatments, including heat shock. For instance, the long-lived daf-2(lf) mutant is highly tolerant to heat shock, and this heightened stress resistance is believed to be essential for lifespan extension. FIG. 6A shows survival of lin-14(n179ts) mutants on control bacteria and lin-14(n179ts) on hsf-1(RNAi) bacteria both cultured at 25° C. The data show that the lifespan extension of lin-14(lf) mutant is hsf-1 dependent.

Figure 6B:
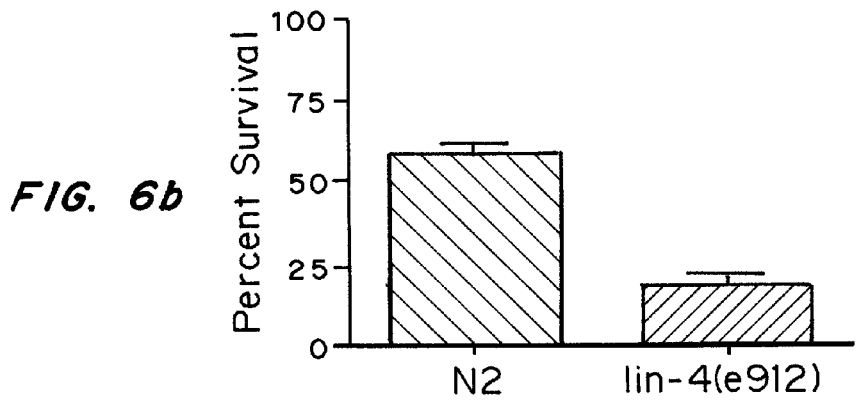
FIGS. 6B and 6C show bar graphs indicating percent survival at 35° C. for lin-4(e912) and lin-14(n-179ts) mutants, respectively.
Figure 6C:
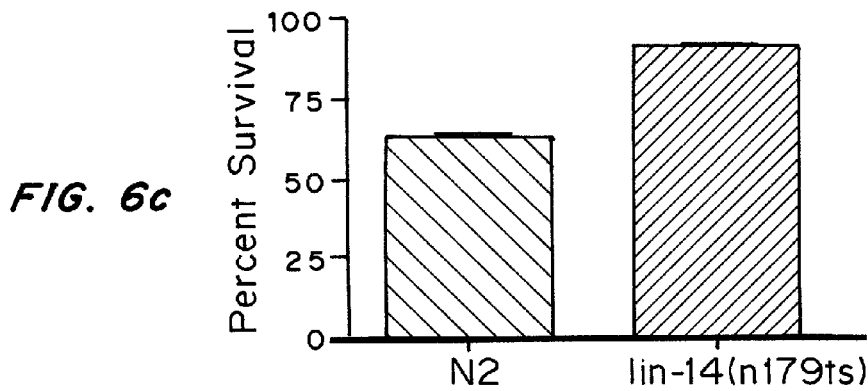

Two-day old adult lin-4(e912) and lin-14(n179ts) were cultured at 20° C. and transferred to 35° C. The animals were scored ten hours after treatment. At least 50 worms were tested for each strain. In accordance with its lifespan phenotype, the lin-4(e912)lf mutant displayed a greater sensitivity to heat shock as compared to wildtype (FIG. 6B), whereas the lin-14(n179)lf mutant displayed a greater resistance to heat shock as compared to wildtype (FIG. 6C).

Figure 3A:
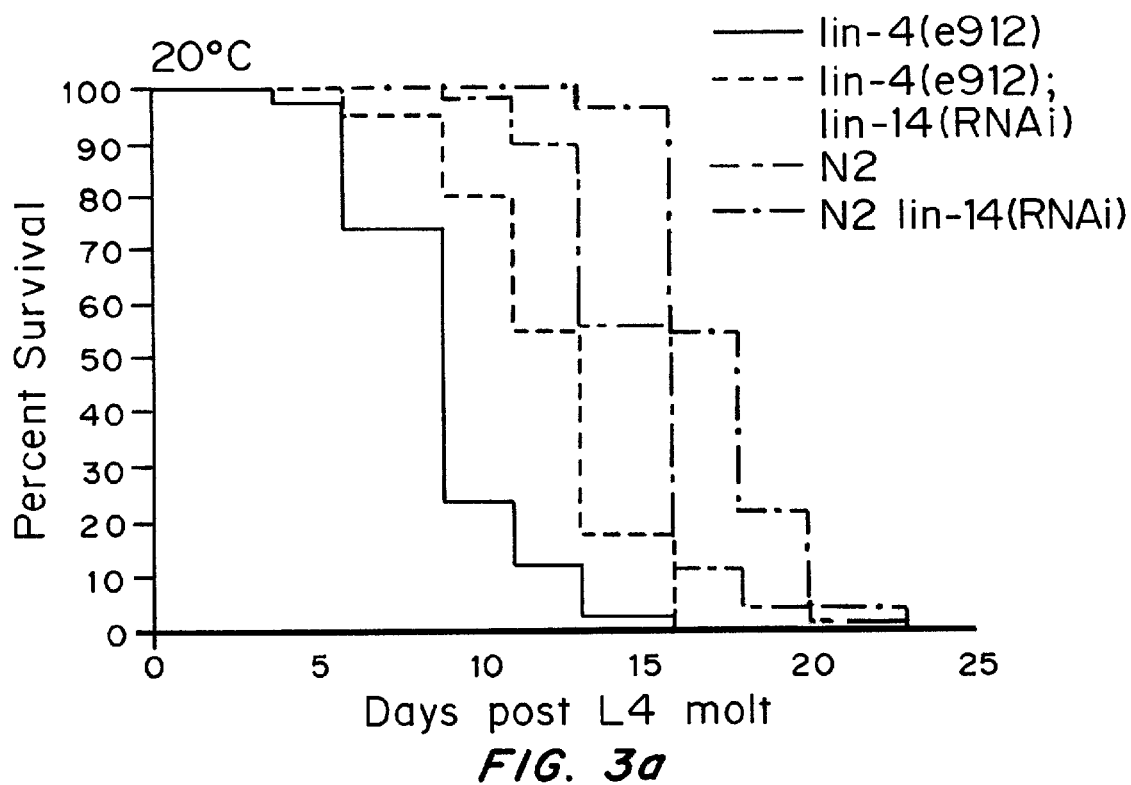
FIGS. 3A and B show line graphs of days versus percent survival for loss of function lin-14 mutations.
Figure 3B:
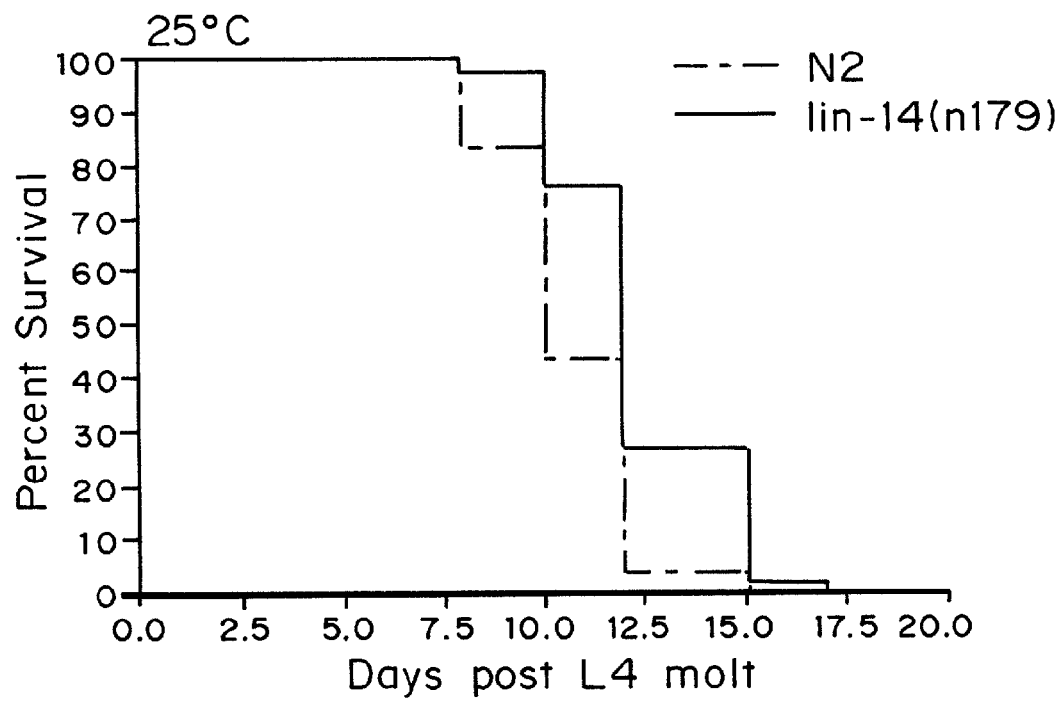

To rule out the possibility that lifespan modulation directed by lin-14 and lin-4 is merely due to their role in larval development, the effect of reducing the function of lin-14 in the post-mitotic adult was examined. RNAi-mediated knockdown of lin-14 after the final larval molt extended the lifespan of wildtype animals, similar to the extension observed when animals were exposed to lin-14(RNAi) just after hatching (FIG. 3A). Additionally, growing the lin-14(n179)lf mutant at the permissive temperature until young adulthood and then shifting to the restrictive temperature also produced an extended lifespan (FIG. 3B). These results demonstrate that lin-14 functions in the adult to restrict lifespan. Furthermore, the short lifespan of the lin-4(e912)lf mutant was also significantly rescued when exposed to lin-14(RNAi) only during adulthood. This result indicates that the lin-4(e912)lf accelerated aging phenotype is not due to developmental abnormalities or an unrelated pleiotropic cause. Thus, the lin-4 miRNA appears to suppress senescence in C. elegans through repression of lin-14 in the adult.

Figure 4A:
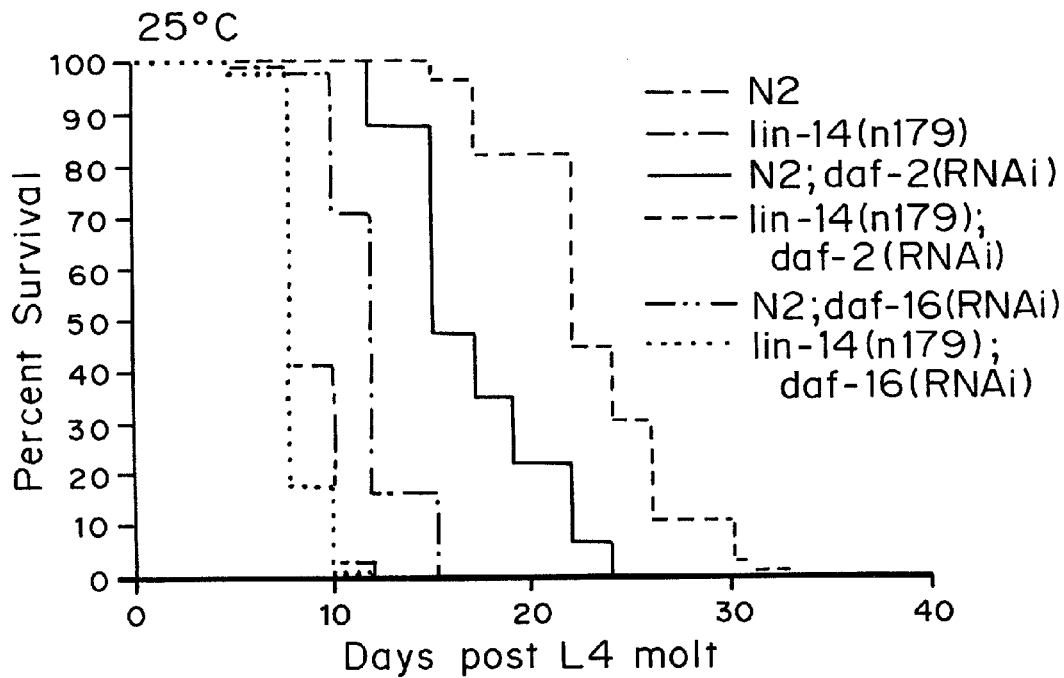
FIGS. 4A-C show line graphs of days versus percent survival for loss of function lin-14 mutations indicating that life-span extension is daf-16 dependent.
Figure 4B:
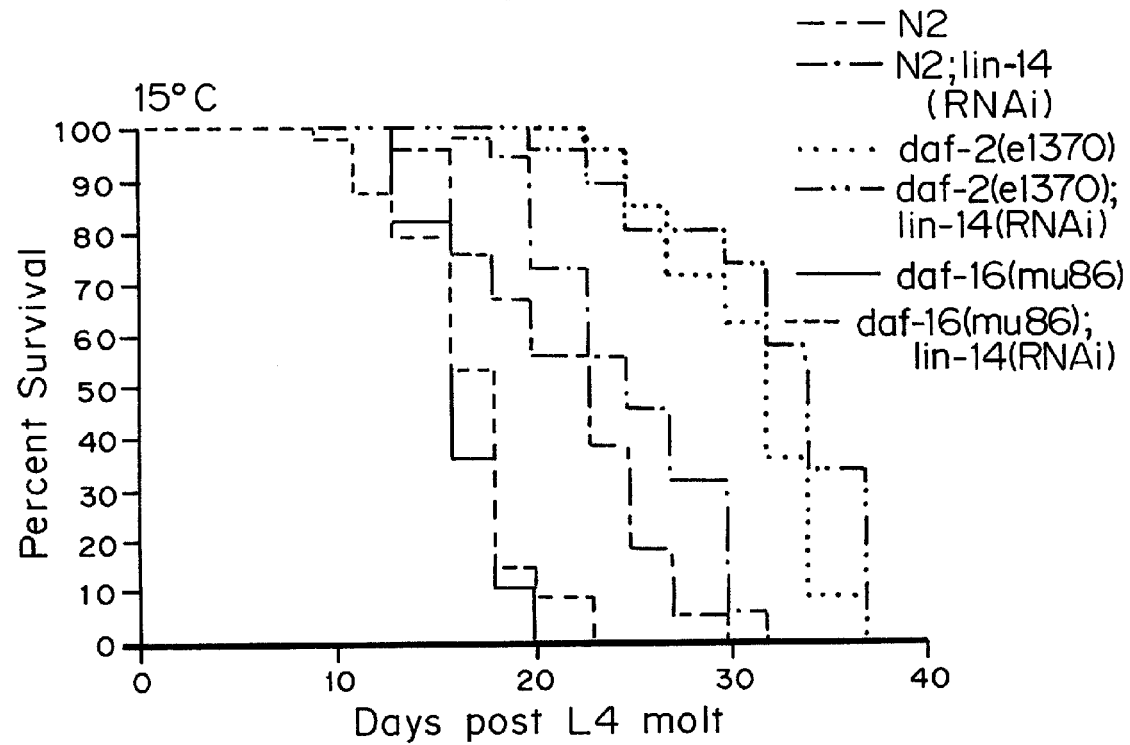

EXAMPLE 4 lin-4 and lin-14 Extend Lifespan by Acting Through the Insulin/IGF-1 Signaling Pathway Several insulin/IGF-1 signaling pathway members regulate lifespan through mechanisms dependent on the downstream DAF-16/FOXO and HSF-1 transcription factors. As with lin-4, inhibiting daf-16 or hsf-1 activity shortens lifespan, whereas elevating their activity lengthens lifespan (Hsu et al., (2003) Science 300, 1142). The daf-16(mu86) null mutant strain, when treated with lin-14(RNAi), did not display an extended lifespan (FIG. 4B), nor did lin-14(n179)lf; daf-16(RNAi) animals (FIG. 4A). These data demonstrate that daf-16 is required for the lin-14(lf) mediated longevity phenotype. lin-4(lf) animals grown on daf-16(RNAi) had shortened lifespan lengths that are identical to that of the lin-4(lf) strain grown on mock RNAi (FIG. 4C), indicating that lin-4 and lin-14 genetically interact with daf-16. However, the lin-4(lf) mutant had a shorter lifespan than the daf-16(lf) mutant, indicating that lin-14 does not exert its effect on lifespan by negative regulation of DAF-16 alone. Consistent with this idea, the lin-14(lf); hsf-1(RNAi) animals had a short lifespan, indicating that the lin-14(lf)-mediated longevity phenotype is dependent on hsf-1 (FIG. 6A) as well as daf-16.

Figure 4C:
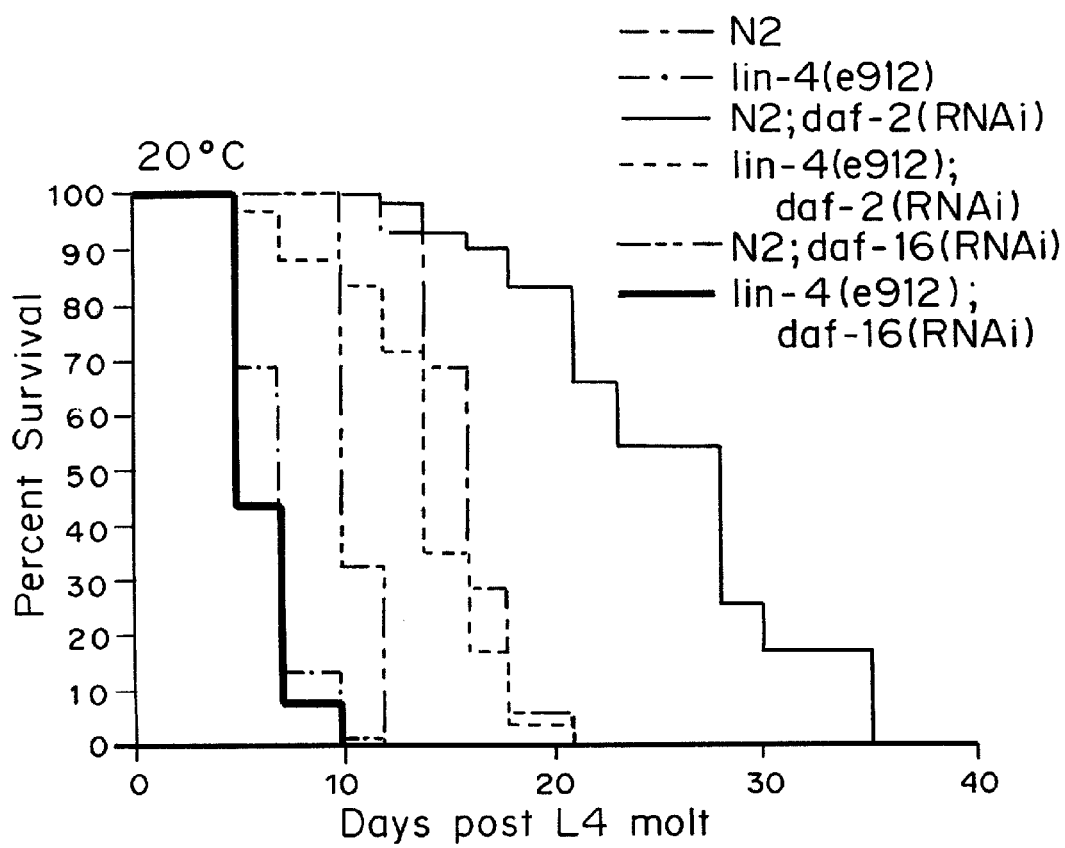

To further explore the possibility that lin-4 and lin-14 might function with the insulin/IGF-1 pathway, interactions with the daf-2-insulin/IGF-1 receptor were analyzed. daf-2 (RNAi) animals had a significant extension in lifespan compared to wildtype animals (FIG. 4C). This lifespan extension was significantly reduced by the lin-4(e912)lf lesion (FIG. 4C), such that lin-4(e912)lf; daf-2(RNAi) animals displayed wildtype lifespans. This phenotype is different from that of the hsf-1(lf) mutation, which wholly abolish the lifespan extension conferred by daf-2(lf) and results in a shortened lifespan. An epistatic relationship between lin-4 and daf-2 cannot be determined as the daf-2 allele is non-null. However, the data suggests that a wildtype copy of daf-2 is necessary for the short lifespan phenotype conferred by lin-4(lf). The lifespan of the daf-2(e1370)lf mutant was modestly extended by lin-14(RNAi) (FIG. 4B), and lin-14(n179)lf; daf-2(RNAi) animals also displayed an extended lifespan as compared to daf-2(RNAi) animals (FIG. 4A). Null alleles were not used for either analysis, and thus concrete epistatic relationships cannot be determined. However, the data support a model where lin-4 and lin-14 modulate lifespan through the canonical daf-2 insulin/IGF-1 pathway. Alternatively, lin-4 and lin-14 may converge onto the DAF-16/FOXO transcription factor in a pathway parallel to the daf-2 insulin/IGF-1 pathway to control aging.

EXAMPLE 5

Heterochronic Mutants Affect Lifespan

Figure 10:
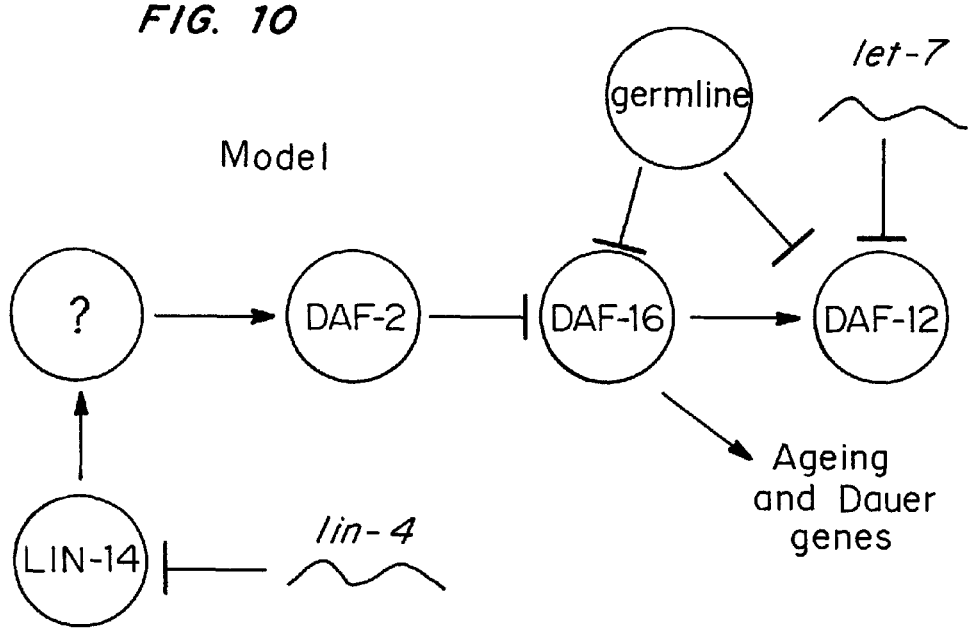
FIG. 10 shows a diagram of an exemplary model for genetic interaction of heterochronic miRNAs with the insulin-signaling pathway to regulate aging in *C. elegans*.

Heterochronic mutants in 15 genes (lin-4, lin-14, daf-12, lin-28, lin-46, lin-X, let-7, alg-1/2, dcr-1, kin-20, lin-42, lin-41, hbl-1, egl-35, lin-29) were subjected to aging assays to determine mean life span. FIG. 10 shows a diagram of an exemplary model for genetic interaction of heterochronic miRNAs with the insulin-signaling pathway to regulate aging in C. elegans.

Figure 7A:
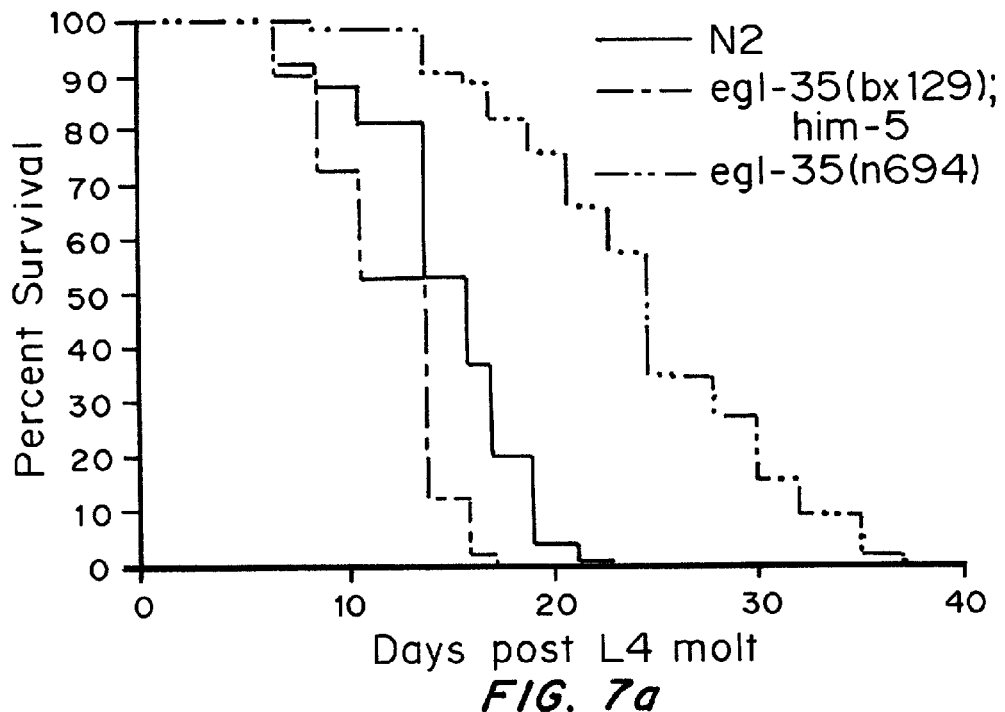
FIGS. 7A-C show line graphs of lifespan analysis of *C. elegans* heterochronic mutants.
Figure 7B:
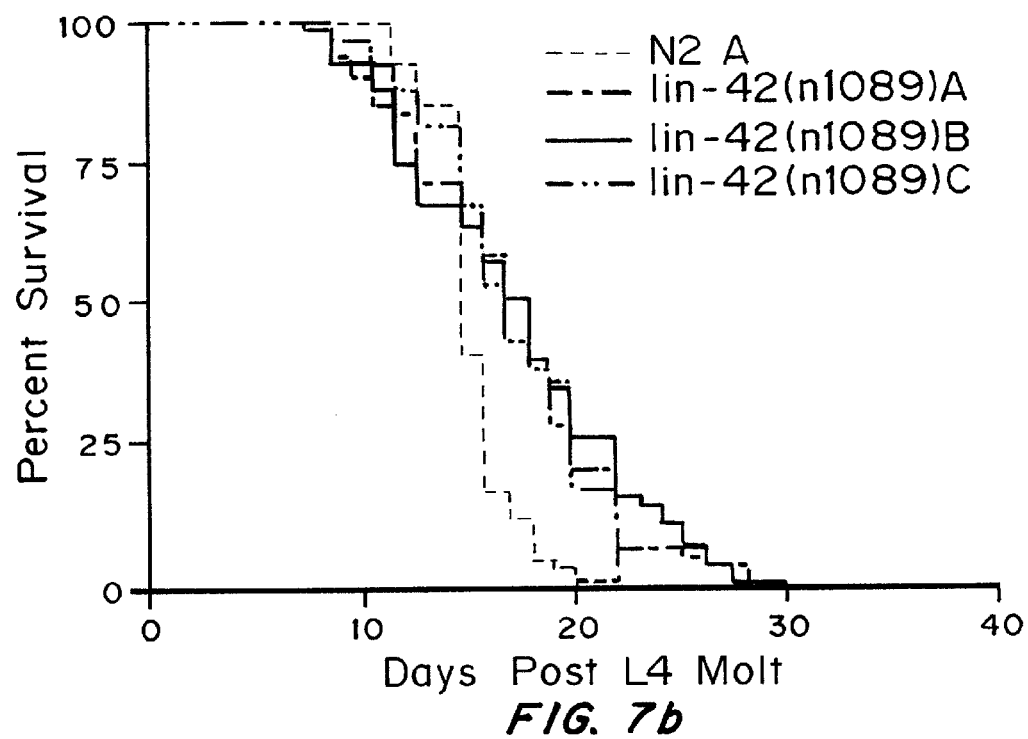
Figure 7C:
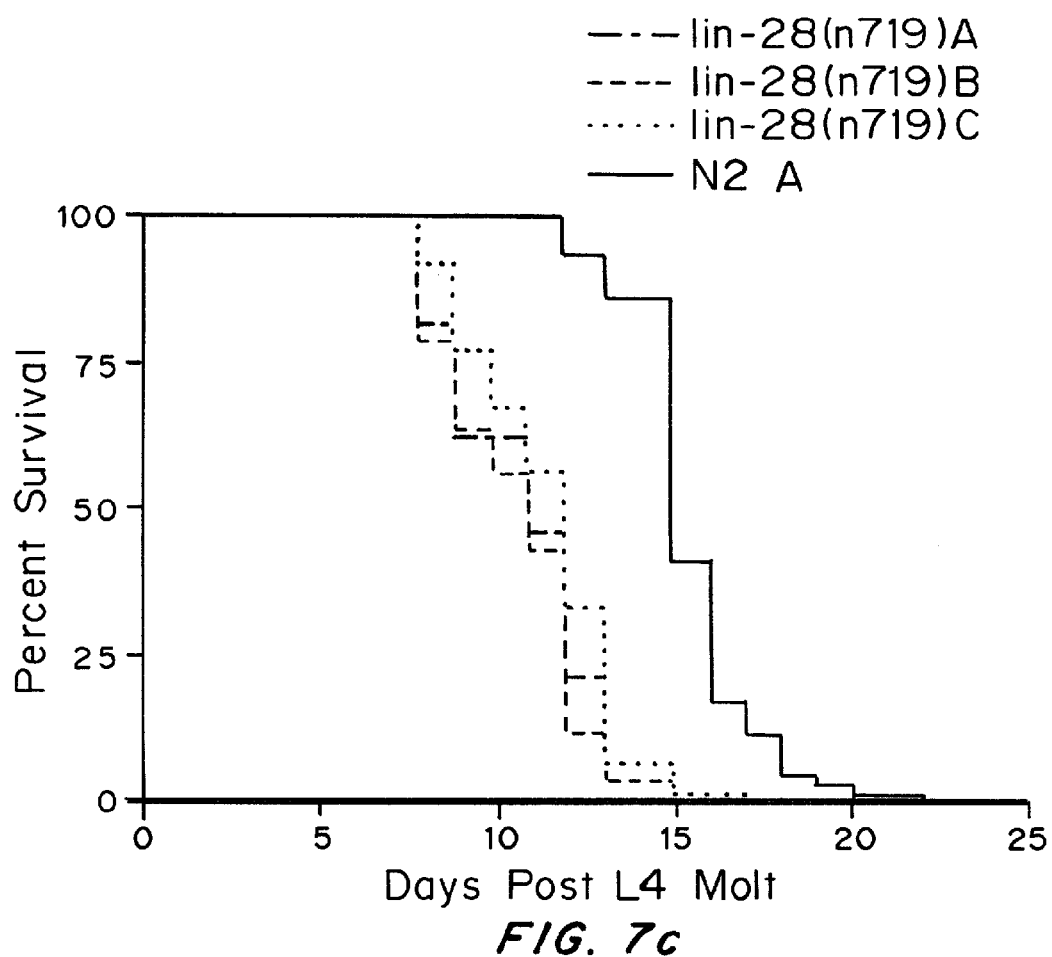
Figure 9:
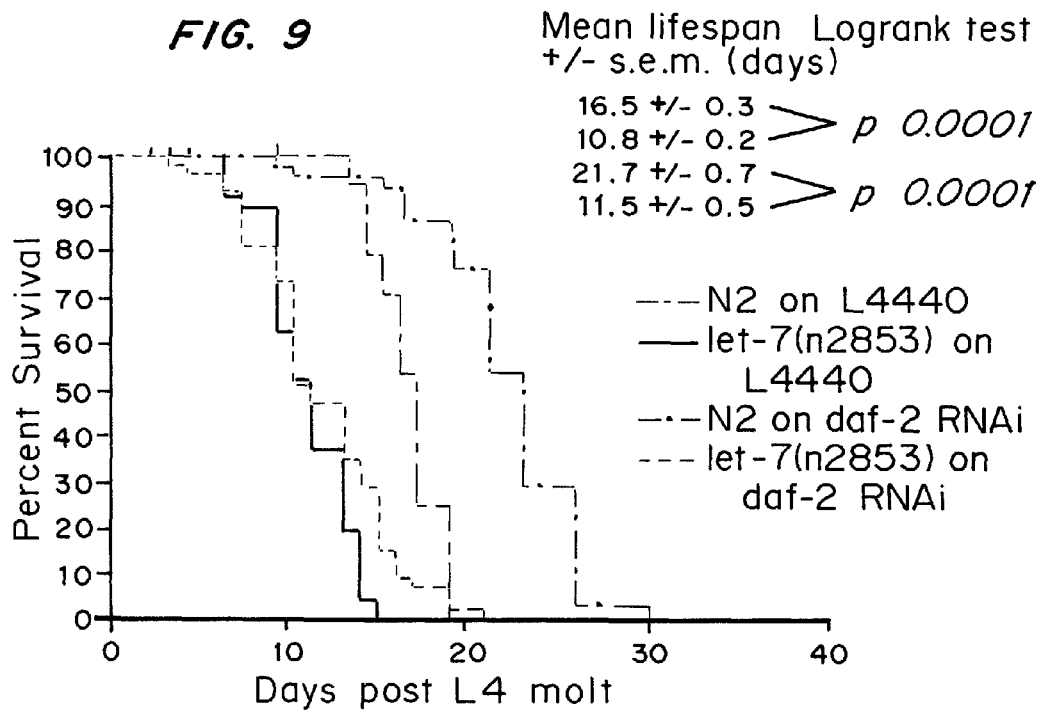
FIG. 9 shows a line graph of days post L4 molt versus percent survival indicating that let-7 is required for the lifespan extending effects of daf-2 mutations.

Assays were performed on animals that are staged and exposed to the chemical 5'-fluorodeoxyuridine (FUDR) after the fourth larval molt to induce sterility. FUDR has previously been shown to not affect lifespan. Each day after attaining adulthood, animals were gently prodded. Lack of movement after prodding indicated death. Repeated assays indicated that lin-42, lin-28, let-7, lin-14, lin-4 and egl-35, affected mean lifespan when perturbed. Three mutants, lin-42 (n1089), egl-35(n694) and lin-14(n179)ts, displayed long-lived phenotypes, while the other 5 mutants, lin-28(n719), lin-4(e912), egl-35(bx129) and two let-7 lf mutants, mg279 and n2853ts, displayed short-lived phenotypes (FIG. 7). let-7(n2853) mutants displayed intense gut autofluorescence at younger stages than wild-type (N2) controls (data not shown). FIG. 9 shows a line graph of days post L4 molt versus percent survival indicating that let-7 is required for the lifespan extending effects of daf-2 mutations.

Figure 11:
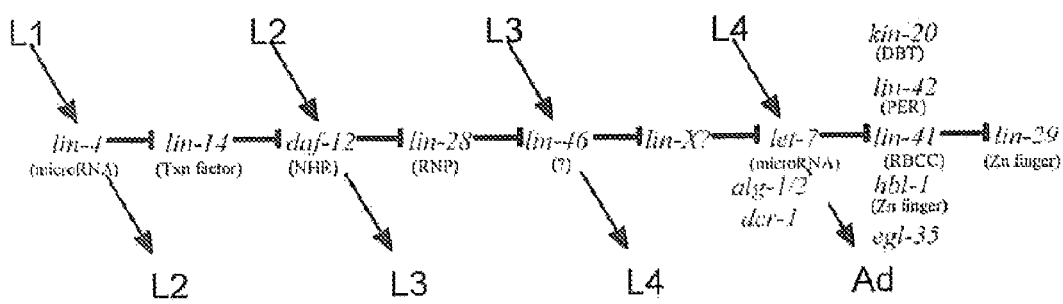
FIG. 11 shows a pathway of genes, termed heterochronic genes (partial list), that regulate timing of developmental transitions in *C. elegans* (L1: larval stage 1; Ad: adult).

Animal's mutant for the 10 remaining heterochronic genes tested showed no altered lifespan. This data reinforces the idea that other heterochronic genes affect timing of aging. These genes include the let-7 miRNA, with multiple human homologues. egl-35 and lin-42 encode transcription factors with human homologues, while lin-28 encodes a zinc-finger containing protein, thought to be an RNA binding protein (also with human homologues. FIG. 11 shows a pathway of genes, termed heterochronic genes (partial list), that regulate timing of developmental transitions in C. elegans (L1: larval stage 1; Ad: adult)

EXAMPLE 6

Statistical Analysis of Lifespan Assays

Table 1 provides a statistical analysis of the lifespan assays described in the previous Examples. The analysis was performed as described above.

TABLE 1

Statistical analysis of lifespan assays

| Strain | Mean +/- s.e.m. (days) ♦ | Number of animals♣ | P ♦ |
|---|---|---|---|
| FIG. 1A at 20° C. | | | |
| N2 (vector control) | 14.6 +/- 0.3 | 69 | |
| lin-4(e912) (control) | 6.9 +/- 0.2 | 56 | <0.0001* |
| N2; lin-14(RNAi) | 18.7 +/- 0.4 | 68 | <0.0001* |
| lin-4(e912); lin-14(RNAi) | 16.6 +/- 0.3 | 72 | <0.0001# |
| FIG. 1B at 25° C. | | | |
| N2 | 9.5 +/- 0.2 | 57 | |
| lin-14(n179ts) | 12.5 +/- 0.3 | 58 | <0.0001* |
| lin-4(e912); lin-14(n179ts) | 9.0 +/- 0.2 | 51 | 0.0906* |
| FIG. 1C at 20° C. | | | |
| N2 | 15.5 +/- 0.5 | 47 | |
| lin-4 overexpression line 1.5 | 18.7 +/- 0.7 | 23 | 0.0004* |
| lin-4 overexpression line 7.4 | 17.0 +/- 0.4 | 74 | 0.0257* |

TABLE 1-continued

Statistical analysis of lifespan assays

| Strain | Mean +/- s.e.m. (days) ♦ | Number of animals♣ | P ♦ |
|---|---|---|---|
| FIG. 1D at 20° C. | | | |
| N2 | 15.9 +/- 0.3 | 59 | |
| lin-4(e912) | 7.7 +/- 0.4 | 85 | <0.0001* |
| lin-14(n355gf) | 5.9 +/- 0.2 | 94 | <0.0001* |
| FIG. 3A at 20° C. | | | |
| N2 (vector control) | 14.8 +/- 0.3 | 55 | |
| N2; lin-14(RNAi) | 17.6 +/- 0.3 | 55 | <0.0001* |
| lin-4(e912) (vector control) | 9.0 +/- 0.4 | 43 | |
| lin-4(e912); lin-14(RNAi) | 12.1 +/- 0.4 | 40 | <0.0001# |
| FIG. 3B at 15° C., then 25° C. at larval to adult transition | | | |
| N2 (vector control) | 10.7 +/- 0.3 | 48 | |
| lin-14(n179ts) | 12.4 +/- 0.3 | 53 | <0.0001* |
| FIG. 4A at 25° C. | | | |
| N2 (vector control) | 8.9 +/- 0.2 | 60 | |
| lin-14(n179ts) (vector control) | 11.9 +/- 0.2 | 56 | <0.0001* |
| N2; daf-2(RNAi) | 17.1 +/- 0.5 | 58 | |
| lin-14(n179ts); daf-2(RNAi) | 23.0 +/- 0.5 | 56 | <0.0001* |
| N2; daf-16(RNAi) | 8.3 +/- 0.1 | 55 | |
| lin-14(n179ts); daf-16(RNAi) | 8.4 +/- 0.1 | 54 | 0.9330* |
| FIG. 4B at 15° C. | | | |
| N2 (vector control) | 21.6 +/- 0.7 | 45 | |
| N2; lin-14(RNAi) | 25.1 +/- 0.6 | 51 | 0.0003* |
| daf-2(e1370) (vector control) | 32.3 +/- 0.8 | 49 | |
| daf-2(e1370); lin-14(RNAi) | 31.1 +/- 0.6 | 53 | 0.0100# |
| daf-16(mu86) (vector control) | 16.4 +/- 0.4 | 28 | |
| daf-16(mu86); (lin-14(RNAi) | 16.7 +/- 0.5 | 42 | 0.2300# |
| FIG. 4C at 20° C. | | | |
| N2 (vector control) | 16.0 +/- 03 | 70 | |
| lin-4(e912) (vector control) | 6.8 +/- 0.2 | 52 | <0.0001* |
| N2; daf-2(RNAi) | 25.5 +/- 0.8 | 67 | |
| lin-4(e912); daf-2(RNAi) | 13.8 +/- 0.5 | 55 | <0.0001* |
| N2; daf-16(RNAi) | 10.7 +/- 0.1 | 64 | |
| lin-4(e912); daf-16(RNAi) | 6.1 +/- 0.2 | 55 | <0.0001* |

*Compared to N2 animals with similar treatment. Experiments were conducted in parallel.
Compared to same strain or control bacteria. Experiments were conducted in parallel.

♣Animals that crawled off plate, burst or bagged were excluded from the total number of animals assayed and all analysis.
♦ All statistical analysis and the determination of mean lifespan length were carried out using Graphpad Prism 4.0 software. The logrank or Mantel-Cox test was used to test the hypothesis that survival curves between experiment and control animals cultured and transferred to new plates in parallel were equal. P values were calculated for individual experiments, consisting of control and experimental animals.

It is understood that the disclosed invention is not limited to the particular methodology, protocols, and reagents described as these may vary. It is also be to understood that the terminology used herein is for the purpose of describing particular embodiments only, and is not intended to limit the scope of the present invention which will be limited only by the appended claims. Those skilled in the art will recognize, or be able to ascertain using no more than routine experimentation, many equivalents to the specific embodiments of the invention described herein. Such equivalents are intended to be encompassed by the following claims.

We claim:

1. A method for altering the insulin-like signaling pathway in a cell comprising
    contacting the cell with an effective amount of an miRNA or a nucleic acid encoding an miRNA to alter the insulin-like signaling pathway,
    wherein the miRNA is selected from the group consisting of let-7, lin-4, mi-125a, mi-125b, combinations, or homologues thereof.

2. The method of claim 1 wherein the miRNA is encoded by a nucleic acid.

3. The method of claim 2 wherein the miRNA is expressed from a vector.

4. The method of claim 3 wherein the vector is selected from the group consisting of a plasmid, cosmid, phagemid, and virus.

5. The method of claim 3 wherein the vector comprises one or more in vivo expression elements.

6. The method of claim 5 wherein the in vivo expression element is selected from the group consisting of a promoter, enhancer, and combinations thereof.

7. The method of claim 1 for altering survivability of a cell comprising
    administering to the cell an miRNA or a nucleic acid encoding an miRNA in an effective amount to alter the survivability of a cell,
    wherein the miRNA is selected from the group consisting of let-7, lin-4, mi-125a, mi-125b, combinations, or homologues thereof.

8. The method of claim 1 wherein an effective amount of an miRNA or a nucleic acid encoding an miRNA is administered to the cells of an individual to inhibit the insulin-like signaling pathway involved in an age-related disorder or premature aging.

9. The method of claim 8 wherein the age-related disorder is selected from the group consisting of Alzheimer's, Parkinson's, diabetes, dementia, atherosclerosis, arthritis, stroke, high blood pressure, and heart disease.

10. The method of claim 8 wherein the individual is a human.

11. The method of claim 1, wherein the miRNA is let-7.

12. The method of claim 1, wherein the miRNA is lin-4.

13. The method of claim 1, wherein the miRNA is mi-125a.

14. The method of claim 1, wherein the miRNA is mi-125b.

15. The method of claim 7, wherein the miRNA is let-7.

16. The method of claim 7, wherein the miRNA is lin-4.

17. The method of claim 7, wherein the miRNA is mi-125a.

18. The method of claim 7, wherein the miRNA is mi-125b.

19. The method of claim 1, wherein the miRNA binds to and inhibits expression of one or more of lin-14, lin-28, lin-42, egl-35 or homologues thereof, or the activity of an encoded protein, in the cell.

20. The method of claim 1, wherein the miRNA binds to and inhibits expression of lin-14, or a homologues thereof, or the activity of an encoded protein, in the cell.

21. The method of claim 1, wherein the miRNA binds to and inhibits expression of lin-28, or a homologues thereof, or the activity of an encoded protein, in the cell.

22. The method of claim 1, wherein the miRNA binds to and inhibits expression of lin-42, or a homologues thereof, or the activity of an encoded protein, in the cell.

23. The method of claim 1, wherein the miRNA binds to and inhibits expression of egl-35, or a homologues thereof, or the activity of an encoded protein, in the cell.

24. The method of claim 7, wherein the miRNA binds to and inhibits expression of one or more of lin-14, lin-28, lin-42, egl-35 or homologues thereof, or the activity of an encoded protein, in the cell.

25. The method of claim 7, wherein the miRNA binds to and inhibits expression of lin-14, or a homologues thereof, or the activity of an encoded protein, in the cell.

26. The method of claim 7, wherein the miRNA binds to and inhibits expression of lin-28, or a homologues thereof, or the activity of an encoded protein, in the cell.

27. The method of claim 7, wherein the miRNA binds to and inhibits expression of lin-42, or a homologues thereof, or the activity of an encoded protein, in the cell.

28. The method of claim 7, wherein the miRNA binds to and inhibits expression of egl-35, or a homologues thereof, or the activity of an encoded protein, in the cell.

* * * * *

UNITED STATES PATENT AND TRADEMARK OFFICE
CERTIFICATE OF CORRECTION

| | | |
|---|---|---|
| PATENT NO. | : 8,354,384 B2 | Page 1 of 1 |
| APPLICATION NO. | : 11/426292 | |
| DATED | : January 15, 2013 | |
| INVENTOR(S) | : Slack et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1086 days.

Signed and Sealed this
Second Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,354,384 B2 | Page 1 of 1 |
| APPLICATION NO. | : 11/426292 | |
| DATED | : January 15, 2013 | |
| INVENTOR(S) | : Frank J. Slack and Michelle M. Boehm | |

It is certified that error appears in the above-identified patent and that said Letters Patent is hereby corrected as shown below:

In the Specification,

Column 1, lines 13-16, replace "The Federal Government has certain rights in this invention by virtue of Grant No. GM647701 from the National Institute of Health to Frank J. Slack and Grant No. DO1119 from the National Science Foundation to Frank J. Slack." with --This invention was made with government support under GM064701 awarded by National Institutes of Health and under 0344429 awarded by National Science Foundation. The government has certain rights in the invention.--.

In the Claims,

Claim 20, column 50, line 36, replace "homologues" with --homologue--.
Claim 21, column 50, line 39, replace "homologues" with --homologue--.
Claim 22, column 50, line 42, replace "homologues" with --homologue--.
Claim 23, column 50, line 45, replace "homologues" with --homologue--.
Claim 25, column 50, line 52, replace "homologues" with --homologue--.
Claim 26, column 50, line 55, replace "homologues" with --homologue--.
Claim 27, column 50, line 58, replace "homologues" with --homologue--.
Claim 28, column 50, line 61, replace "homologues" with --homologue--.

Signed and Sealed this
Nineteenth Day of May, 2015

Michelle K. Lee
*Director of the United States Patent and Trademark Office*

UNITED STATES PATENT AND TRADEMARK OFFICE
CERTIFICATE OF CORRECTION

PATENT NO. : 8,354,384 B2
APPLICATION NO. : 11/426292
DATED : January 15, 2013
INVENTOR(S) : Frank J. Slack and Michelle M. Boehm Page 1 of 1

It is certified that error appears in the above-identified patent and that said Letters Patent is hereby corrected as shown below:

In the Specification

Column 1, Lines 13-16, replace "The Federal Government has certain rights in this invention by virtue of Grant No. GM647701 from the National Institute of Health to Frank J. Slack and Grant No. DO 1119 from the National Science Foundation to Frank J Slack." with "This invention was made with government support under GM064701 awarded by National Institutes of Health and under 0344429 awarded by National Science Foundation. The government has certain rights in the invention."

This certificate supersedes the Certificate of Correction issued May 19, 2015.

Signed and Sealed this
Twenty-third Day of June, 2020

Andrei Iancu
*Director of the United States Patent and Trademark Office*